(12) United States Patent
Saddiq et al.

(10) Patent No.: US 10,251,842 B1
(45) Date of Patent: Apr. 9, 2019

(54) NANOCAPSULE CONTAINING A BIOACTIVE COMPOUND, AND A METHOD OF REDUCING TOXICITY RESULTING FROM CANCER THERAPY

(71) Applicant: King Abdulaziz University, Jeddah (SA)

(72) Inventors: Amna Ali Nasser Saddiq, Jeddah (SA); Shaker Ahmad Mousa, Rensselaer, NY (US); Deena Shaker Mousa, Wynantskill, NY (US)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 15/802,015

(22) Filed: Nov. 2, 2017

(51) Int. Cl.
| | | |
|---|---|---|
| *A61K 33/24* | (2006.01) | |
| *A61K 9/48* | (2006.01) | |
| *A61P 25/02* | (2006.01) | |
| *A61P 13/12* | (2006.01) | |
| *A61K 31/404* | (2006.01) | |
| *A61K 31/704* | (2006.01) | |
| *A61K 31/366* | (2006.01) | |
| *A61P 35/00* | (2006.01) | |

(52) U.S. Cl.
CPC .......... *A61K 9/4816* (2013.01); *A61K 31/366* (2013.01); *A61K 31/404* (2013.01); *A61K 31/704* (2013.01); *A61K 33/24* (2013.01); *A61P 13/12* (2018.01); *A61P 25/02* (2018.01); *A61P 35/00* (2018.01)

(58) Field of Classification Search
CPC ............ A61K 47/6925; A61K 49/0093; A61K 31/475
See application file for complete search history.

(56) References Cited

U.S. PATENT DOCUMENTS

| 8,858,995 B2 | 10/2014 | Gupta et al. |
|---|---|---|
| 2013/0129809 A1 | 5/2013 | Srivastava et al. |
| 2013/0209578 A1* | 8/2013 | Borden .............. A61K 31/7056 424/649 |
| 2016/0263047 A1* | 9/2016 | Kaufman .............. A61K 9/0014 |

FOREIGN PATENT DOCUMENTS

IN 20060169111 2/2008

OTHER PUBLICATIONS

The Benefits of DIM [online] retrieved from: http://fortwaynephysicalmedicine.com/blog/the-benefits-of-dim; Aug. 2014 5 pages, (Year: 2014).*
Locatelli et al. (J Nanopart Res 2012;14:1316 pp. 1-17) (Year: 2012).*
"Nanoencapsulation of Bioactive Compounds for the Treatment of Pancreatic Cancer", Google Science Fair, https://www.googlesciencefair.com/projects/en/2014/5e70bdf76b109c8fdfd227f78803e1b3cf1c65ad0d207f2ed094c3c8a1564f34, Oct. 18, 2016, pp. 1-14.

(Continued)

*Primary Examiner* — Ernst V Arnold
(74) *Attorney, Agent, or Firm* — Oblon, McClelland, Maier & Neustadt, L.L.P.

(57) ABSTRACT

Nanocapsules of bioactive compounds derived from natural products as an adjunct treatment for cancer. Nanocapsules of bioactive compounds showed synergy in the treatment of cancer therapy-induced toxicity.

18 Claims, 19 Drawing Sheets

(56) References Cited

OTHER PUBLICATIONS

Amit B. Shirode, et al., "Nanoencapsulation of pomegranate bioactive compounds for breast cancer chemoprevention", International Journal of Nanomedicine, vol. 10, No. 1, Jan. 9, 2015, pp. 475-484.

Mouad Edderkaoui, et al., "Ellagic acid induces apoptosis through inhibition of nuclear factor κB in pancreatic cancer cells", World Journal of Gastroenterology, vol. 14, No. 23, Jun. 21, 2008, pp. 3672-3680.

Min Zhao, et al., "Ellagic acid inhibits human pancreatic cancer growth in Balb c nude mice", Cancer Letters, vol. 337, Issue 2, Sep. 1, 2013, pp. 210-217 (Abstract only).

* cited by examiner

Control (Matrigel, M)

(M)+ Pancreatic Cancer (PC)

M+PC+ (Ellagic Acid, EA)

M+PC +(Diindolylmethane, DIM)

M+PC+ (EA + DIM)

M+PC+ (EA NP + DIM NP)

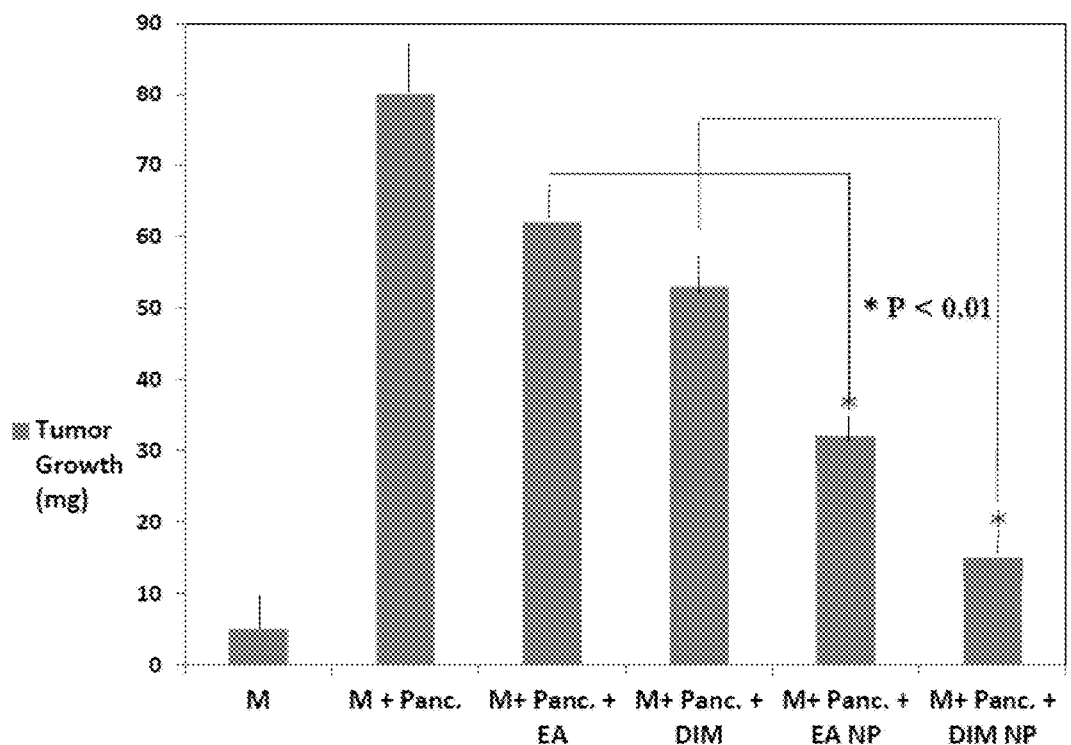

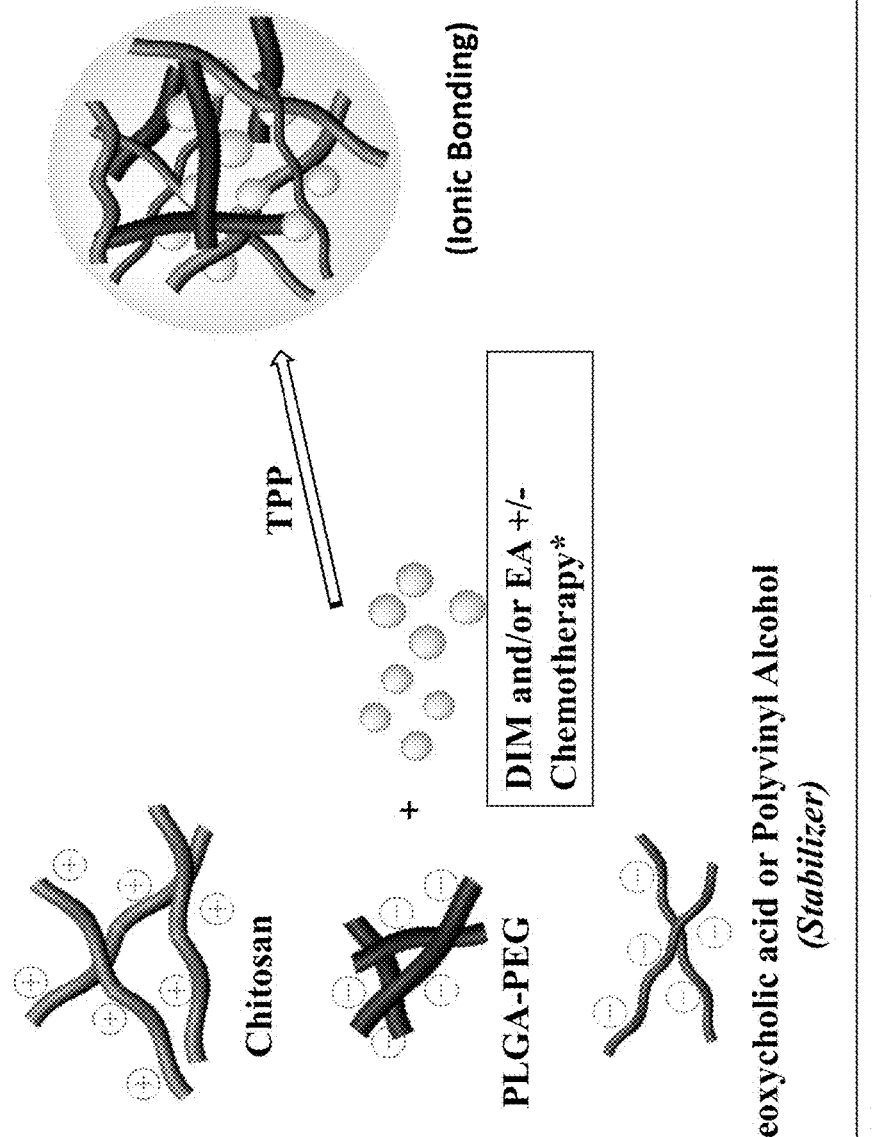

Size measurement: Void PLGA-PEG-NPs, average size of 141.7 nm

Size distribution of 3 repeats of PLGA [70% Lactic Acid: 30% Glycolic Acid]-PEG dissolved in DMSO + 1% Deoxycholic Acid as stabilizer and encapsulating Tomozolomide (TMZ)

Zeta potential for 3 repeats of PLGA [70% Lactic Acid: 30% Glycolic Acid]-PEG dissolved in DMSO + 1% PVA as stabilizer Zeta Potential: PLGA-PEG-TMZ-NPs, with zeta potential -3.8 mv, which is shifted to positive mv upon addition Chitosan (+10 to +30 mv)

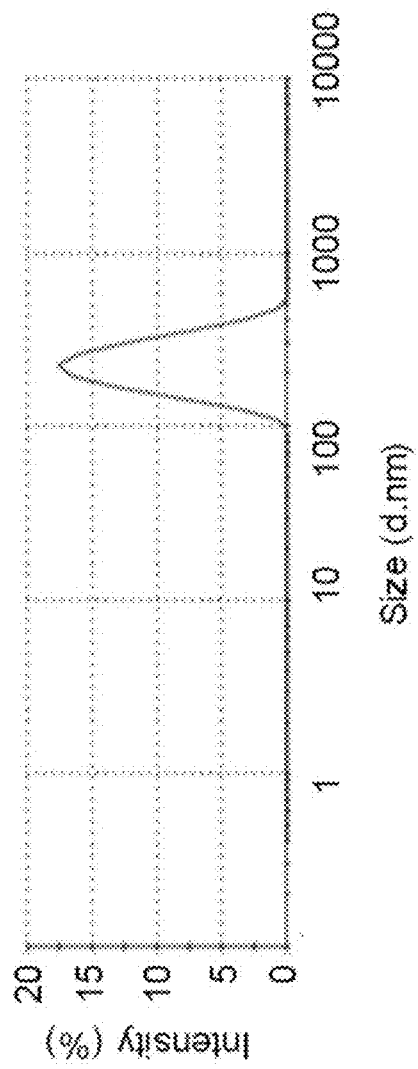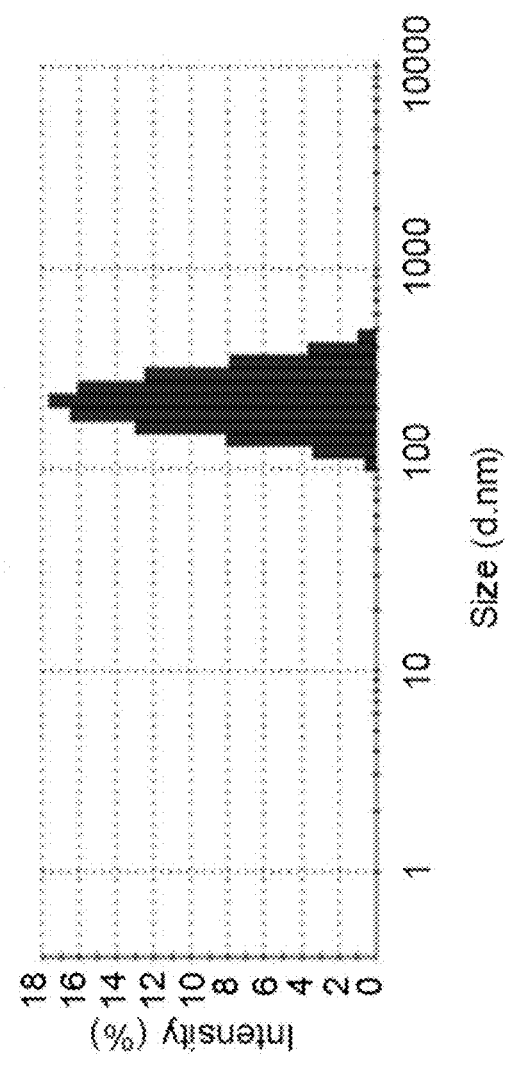
FIG. 10G
FIG. 10H

NANOCAPSULE CONTAINING A BIOACTIVE COMPOUND, AND A METHOD OF REDUCING TOXICITY RESULTING FROM CANCER THERAPY

BACKGROUND

Field of the Disclosure

The presently-disclosed subject matter relates a nanocapsule containing one or more bioactive compounds and optional anticancer agents. Further, the presently-disclosed subject matter relates to methods for treating cancer and toxicity resulting from cancer therapy such as chemotherapy.

Description of the Related Art

Pancreatic carcinoma and glioma carries the highest fatality rate among all human cancers (Hidalgo M. Pancreatic cancer. N Engl J Med. 2010; 362(17): 1605-1617, incorporated herein by reference in its entirety). Reasons for low survival include aggressive tumors, high metastatic potential, and late presentation at the time of diagnosis. Despite the introduction of gemcitabine and attempts at developing combination chemotherapy regimens, pancreatic cancer remains highly aggressive and chemo-resistant, and there is a need for improved methods to treat it. Similarly, glioblastoma still is fatal with poor survival and high mortality outcome despite treating with various anticancer agents, such as temozolomide, and other recent strategies.

Cruciferous vegetables, such as broccoli, brussel sprouts, cabbage, and kale, contain bioactive compounds that have demonstrated anticancer efficacy against various cancer types. However, these bioactive compounds, such as diindolymethane (DIM), ellagic acid (EA), and sulforaphane, are insoluble or unstable (Wang T T, Schoene N W, Milner J A, Kim Y S. Broccoli-derived phytochemicals indole 3-carbinol and 3,3'-diindolylmethane exerts concentration-dependent pleiotropic effects on prostate cancer cells: comparison with other cancer preventive phytochemicals. Mol. Carcinog. 2012 March; 51(3):244-56; Durgo K, Belščak-Cvitanorić A, Stančič A, Franekić J, Domes D. The bioactive potential of red raspberry (Rubus idaeus L.) leaves in exhibiting cytotoxic and cytoprotective activity on human laryngeal carcinoma and colon adenocarcinoma. J Med Food. 201 March; 15(3):258-68; and Houghton C A, Fassett R G, Coombes J S. Sulforaphane: translational research from laboratory bench to clinic. Nutr Rev. 2013 November; 71(11):709-26, each incorporated herein by reference in their entirety).

Therefore, it is an objective of the present disclosure to provide encapsulated bioactive compounds for cancer therapy. The encapsulated bioactive compounds may be used with chemotherapeutic agents.

SUMMARY OF THE INVENTION

A first aspect of the disclosure relates to a nanocapsule, comprising: (i) 0.01-10 wt % of at least one bioactive compound selected from the group consisting of curcumin, a green tea polyphenol, punicalagin, diindolylmethane, oltipraz, tocotrienol, tocopherol, plumbagin, cyanidin, delphinidin, lycopene, lupeol, curcurbitacin-B, withaferin A, indole-3-carbinol, genestein, resveratrol, co-enzyme Q-10, ellagic acid, petunidin, malvidin, peonidin, and sulforaphane, based on a total weight of the nanocapsule; and (ii) a biocompatible polymer encapsulating the bioactive compound, wherein an average diameter of the nanocapsuleis in a range of 100-500 nm.

In one embodiment, the average diameter of the nanocapsule is in a range of 130-300 nm.

In one embodiment, the average diameter of the nanocapsule is in a range of 150-250 nm.

In one embodiment, the bioactive compound is diindolylmethane, ellagic acid, or both.

In one embodiment, the biocompatible polymer is not polycaprolactone.

In one embodiment, the biocompatible polymer comprises at least one selected from the group consisting of a polylactic-co-glycolic acid) (PLGA), a poly(ethylene glycol) (PEG), a cyclodextrin, a polyvinyl alcohol, deoxycholic acid, a chitosan, and a copolymer thereof.

In one embodiment, the biocompatible polymer comprises polylactic-co-glycolic acid) (PLGA) and poly(ethylene glycol) (PEG).

In one embodiment, the biocompatible polymer is a diblock copolymer of poly(lactic-co-glycolic acid) (PLGA) and poly(ethylene glycol) (PEG) or an alternating multi-block copolymer of polylactic-co-glycolic acid) (PLGA) and poly(ethylene glycol) (PEG).

A second aspect of the disclosure relates to a method for treating neuropathy and/or nephrotoxicity associated with chemotherapy, comprising administrating an effective amount of at least one bioactive compound selected from the group consisting of curcumin, a green tea polyphenol, punicalagin, diindolylmethane, oltipraz, tocotrienol, tocopherol, plumbagin, cyanidin, delphinidin, lycopene, lupeol, curcurbitacin-B, withaferin indole-3-carbinol, genestein, resveratrol, co-enzyme Q-10, ellagic acid, quercetin, petunidin, malvidin, peonidin, and sulforaphane, which is encapsulated by a biocompatible polymer, to a subject m need thereof.

In one embodiment, the chemotherapy comprises administering an effective amount of a platinum-based anticancer agent to the subject.

In one embodiment, the platinum-based anticancer agent is at least one of cisplatin, carboplatin, and oxaliplatin. In this embodiment, the cancer may be bladder cancer and/or ovarian cancer.

In one embodiment the effective amount of the bioactive compound is in a range of 0.1-300 mg/kg body weight of the subject.

In one embodiment, the bioactive compound is at least one selected from the group consisting of curcumin, green tea polyphenols (e.g., epigallocatechin gallate), punicalagin, diindolylmethane, oltipraz, tocotrienol, tocopherol, plumbagin, cyanidin, delphinidin, lycopene, lupeol, curcurbitacin-B, withaferin A, indole-3-carbinol, genestein resveratrol, quercetin, co-enzyme Q-10, ellagic acid, petunidin, peonidin, sulforaphane, and fennel extract.

In one embodiment, the bioactive compound is diindolylmethane, ellagic acid, or both.

In one embodiment, the biocompatible polymer comprises at least one selected from the group consisting of a polylactic-co-glycolic acid) (PLGA), a poly(ethylene glycol) (PEG), a cyclodextrin, a polyvinyl alcohol, deoxycholic acid, a chitosan, and a copolymer thereof.

In one embodiment, the biocompatible polymer comprises poly(lactic-co-glycolic acid) (PLGA) and poly(ethylene glycol) (PEG).

A third aspect of the disclosure relates to a method for treating cancer, comprising administrating an effective amount of diindolymethane, ellagic acid, or both, which is encapsulated by a biocompatible polymer, and an effective amount of an anticancer agent to a subject in need thereof, wherein the administrating does not cause neuropathy, nephrotoxicity, and/or cardiotoxicity in the subject.

In one embodiment, the anticancer agent is cisplatin and/or doxorubicin.

In one embodiment, the cancer is at least one selected from the group consisting of pancreatic cancer, colon cancer, glioma, and breast cancer.

In one embodiment, the biocompatible polymer comprises at least one selected from the group consisting of a poly(lactic-co-glycolic acid), a polyethylene glycol), a cyclodextrin, a polyvinyl alcohol, deoxycholic acid, a chitosan, and a copolymer thereof.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 6 shows the effect of unencapsulated DIM, unencapsulated EA, nanocapsules containing PLGA-PEG and DIM (DIM NP), and nanocapsules containing PLGA-PEG and EA. (EA NP) on the pancreatic tumor growth in the CAM model after 3 days of incubation of controlled humidity and air conditions.

FIG. 9A illustrates the synthesis of nanocapsules containing diindolymethane (DIM) and/or ellagic acid (EA), optional anticancer agents, and PLEG-PEG bridged with chitosan and stabilized using deoxycholic acid or polyvinyl alcohol (PVA) via an ionic bonding using sodium tripolyphosphate (TTP).

FIG. 10G shows the size distribution of nanocapsules containing poly(D,L-lactic-co-glycolic acid)-polyethylene glycol (PLEA-PEG), chitosan, and diindolylmethane (DIM).

FIG. 10H shows the size distribution of nanocapsules containing poly(D,L-lactic-co-glycolic acid)-polyethylene glycol (PLEA-PE) chitosan, and diindolylmethane (DIM).

DETAILED DESCRIPTION OF THE EMBODIMENTS

Figure 1A:
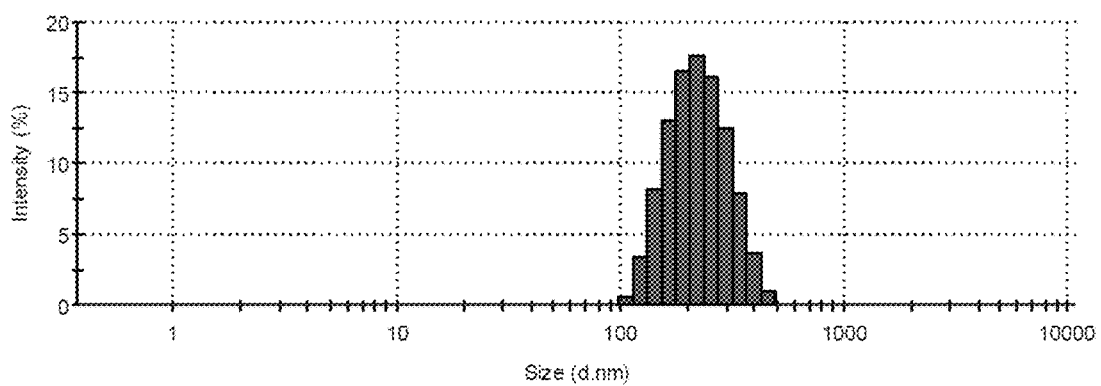
FIG. 1A shows the size distribution of nanocapsules containing poly(D,L-lactic-co-glycolic acid)-polyethylene glycol (PLGA-PEG) and diindolylmethane (DIM).

Embodiments of the present disclosure will now be described more fully hereinafter with reference to the accompanying drawings, which some, but not all f the embodiments of the disclosure are shown.

The present disclosure will be better understood with reference to the following definitions.

As used herein, the words "a" and "an" the like carry the meaning of "one or more". Within the description of this disclosure, where a numerical limit or range is stated, the endpoints are included unless stated otherwise. Also, all values and subranges within a numerical limit or range are specifically included as if explicitly written out.

Although the open-ended terra "comprising," as a synonym of terms such as including, containing, or having, use herein to describe and claim the present nanocapsule and methods, the nanocapsule and/or methods may alternatively be described using more limiting terms, such as "consisting of" or "consisting, essentially of" the recited ingredients/steps. For example, a nanocapsule which consists essentially of the recited ingredients may contain other ingredients which do not adversely affect the stability, anticancer and/or therapeutic properties of the nanocapsule. Although various illustrative embodiments are described herein, any of a number of changes may be made to various embodiments without departing from the scope of the disclosure as described by the claims. For example, the order in which various described method steps are performed may often be changed in alternative embodiments, and in other alternative embodiments one or mote method steps may be skipped altogether.

There is limited evidence of cancer prevention for bioactive compounds derived from natural sources. However, there is a great potential for their utility in cancer patients. Poly-phenols (such as ellagic acid (EA) derived from raspberry, strawberry, pomegranate) and 3,3'-diindolylmethane (also referred to herein as "diindolylmethane"), which is derived from broccoli and cabbage, have poor absorption, low systemic bioavailability, and a short retention time limiting their full chemopreventive potential. Ellagic acid mostly accumulates in intestinal epithelial cells with limited absorption into systemic circulation (Seeram N P, Henning S M, Zhang Y, Suchard M, Li Z, Heber D. Pomegranate juice ellagitannin metabolites are present in human plasma and some persist in urine for up to 48 hours. J Nutr, 2006; 136(10): 2481-5; Cerda, B., F. A. Tomas-Barberan, and J. C. Espin, Metabolism of antioxidant and chemopreventive ellagitannins from strawberries, raspberries, walnuts, and oak-aged wine in humans: identification of biomarkers and individual variability. J Agric Food Chem, 2005; 53(2): p. 227-35; Cerda. B., et al., The potent in vitro antioxidant ellagitannins from pomegranate juice are metabolized into bioavailable but poor antioxidant hydroxy-6H-dibenzopyran-6-one derivatives by the colonic microflora of healthy humans. Eur J Nutr, 2004; 43(4):205-20; and Smart, R C., et al., Disposition of the naturally occurring antimutagenic plant phenol, ellagic acid, and its synthetic derivatives, 3-O-decylellagic acid and 3,3'-di-O-methylellagic acid in mice. Carcinogenesis, 1986; 7(10): p. 1663-7, each incorporated herein by reference in their entirety). As a result, low nanomolar concentrations of free ellagic acid have been detected in human blood after consumption of pomegranate juice (Whitley, A. C., et al., Intestinal epithelial cell accumulation of the cancer preventive polyphenol ellagic acid— extensive binding to protein and DNA. Biochem Pharmacol, 2003; 66(6):907-15 incorporated herein by reference in its entirety). In addition, absorbed ellagic acid has a short half-life due to rapid metabolism in the liver and excretion through the urine (Seeram, N. P., R. Lee. and D. Heber, Bioavailability of ellagic acid in human plasma after consumption of ellagitannins from pomegranate (Punica granatum L.) juice. Clin Chim Acta, 2004; 348(1-2):63-8, incorporated herein by reference in its entirety).

Encapsulation of ellagic acid and/or diindolylmethane into biocompatible and biodegradable nanocapsules may overcome their susceptibility to gastrointestinal hydrolysis, poor absorption, low systemic bioavailability, and a short half-life. Encapsulation of cancer drugs was explored to decrease toxicity, while increasing stability, bioavailability, and allowing for selective tumor uptake of cancer drugs (Bharali D J and Mousa S A. Emerging nanomedicines for early cancer detection and improved treatment: current perspective and future promise. Pharmacol Ther, 2010; 128(2):324-35; Siddiqui I A, Adhami V M, Bharali D J, Hafeez B B, Asim M, Kliwaja S I, Ahmad N, Cui H, Mousa S A, Mukhtar H. Introducing nanochemoprevention as a novel approach for cancer control: proof of principle with green tea polyphenol epigallocatechin-3-gallate. Cancer Res, 2009; 69(5):1712-6; Bharali D J, Siddiqui I A, Adhami Y M, Chamcheu J C, Aldahmash A M, Mukhtar H, Mousa S A. Nanocapsule delivery of natural products in the prevention and treatment of cancers: Current status and future, prospects. Cancers 2011; 3: 4024-4045; and Sanna V. Siddiqui I A, Sechi M, Mukhtar H. Nanoformulation of natural products for prevention and therapy of prostate cancer. Cancer Left. 2013 Jun. 28; 334(1):142-51, each incorporated herein by reference their entirety).

Nanocapsules containing poly(D,L-lactic-co-glycolic acid) (PLGA) are biocompatible, biodegradable, and stable in biological fluids. These nanocapsules protect the encapsulated compounds from degradation and allow for their sustained release (Lü J M, Wang X, Marin-Muller C, Wang H, Lin P H, Yao Q, Chen C. Current advances in research and clinical applications of PLGA-based nanotechnology. Expert Rev Mol Diagn, 2009; 9(4): 325-41; and Danhier F, Ansorena E, Silva J M, Coco R, Le Breton A, Préat V. PLGA-based nanocapsules: an overview of biomedical applications. J Control Release, 2012; 161(2): 505-22, each incorporated herein by reference in its entirety). PLGA nanocapsules are taken up by fluid phase pinocytosis and endocytosis (Sah H, Thoma L A, Desu. H R, Sah E, Wood G C. Concepts and practices used to develop functional PLGA-based nanoparticulate systems. International journal of nanomedicine, 2013; 8:747-65, incorporated herein by reference in its entirety). Further, these nanocapsules rapidly escape the endolysosomes and release the encapsulated compounds in the cytoplasm. The PLGA polymer undergoes spontaneous and enzymatic hydrolysis of the ester linkages to produce lactic acid and glycolic acid. As both lactic acid and glycolic acid are endogenous molecules, they are easily metabolized to carbon dioxide and water via the Krebs cycle. The PLGA polymer is known to be safe in humans. The US Food and Drug Administration and European Medicine Agency have approved the use of nanocapsules containing PLGA in the parenteral route are the use of microcapsules containing PLGA in implants. In addition, these nanocapsules are being investigated as oral drug carriers (Kalaria D R, Sharma G, Beniwal V, Ravi Kumar M N. Design of biodegradable nanocapsules for oral delivery of doxorubicins: in vivo pharmacokinetics and toxicity studies in rats. Pharm Res, 2009; 26(3):492-501; Kumar G, Sharma S Shafiq N, Pandhi P, Khuller G K, Malhotra S. Pharmacokinetics and tissue distribution studies of orally administered nanocapsules encapsulated ethionamide used as potential drug delivery system in management of multi-drug resistant tuberculosis. Drug Deliv, 2011; 18(1): 65-73; and He, W. S. W. Horn, and M. D. Hussain, Improved bioavailability of orally administered mifepristone from PLGA nanocapsules. Int J Pharm 2007; 334(1-2):173-8, each incorporated herein by reference in their entirety). A major disadvantage of these nanocapsules is that they are rapidly opsonized by immunoglobulins and complement proteins, and cleared by the reticuloendothelial system. Thus, the nanocapsules may not reach target tissues. Therefore, the presently disclosed nanocapsule includes a copolymer of PLGA and polyethylene glycol (PEG) thereby reducing opsonization and prolonging the circulation time in the blood by several orders of magnitude.

An aspect of the disclosure relates to a nanocapsule, comprising or consisting essentially of at least 0.01 wt %, 0.05 wt %, 0.1 wt %, 0.5 wt %, 1 wt %, 2 wt %, and up to 10 wt %, 9.5 wt %, 9 wt %, 8 wt % 7 wt %, or 6 wt % of at least one bioactive compound, based on a total weight of the nanocapsule; and a biocompatible polymer encapsulating the bioactive compound.

The nanocapsule may preferably be spherical substantially spherical (e.g., oval or oblong shape). In other embodiments, the nanocapsule can be of any shape that provides desired permeability and/or stability of the nanocapsule, and/or release rates of the encapsulated compound (e.g., the bioactive compound). For example, the nanocapsule may be in a form of at least one shape such as a sphere, a rod, and a disc (e.g., a biconcave disc resembling an erythrocyte).

Dispersity is a measure of the heterogeneity of sizes of nanocapsules in a mixture. In probability theory and statistics, the coefficient of variation (CV) also known as relative standard deviation (RSD) is a standardized measure of dispersion of a probability distribution. It is expressed as a percentage and is defined as the ratio of the standard deviation (o) of to the mean (μ, or its absolute value |μ|). The CV or RSD is widely used to express precision and repeatability. It shows the extent of variability in relation to the mean of a population. The nanocapsules having a narrow size dispersion, i.e. monodispersity, is preferred. As used herein, "monodisperse", "monodispersed" and/or "monodispersity" refers to nanocapsules having a CV or RSD of less than 25%, preferably less than 20%.

The nanocapsules may be monodisperse with a coefficient of variation or relative standard deviation (ratio of the particle size standard deviation to the particle size mean) of less than 15%, less than 12%, less than 10%, less than 9%, less than 8%, less than 7%, less than 6%, less than 5%, or preferably less than 2%.

In one embodiment, the nanocapsules are monodisperse and have a particle diameter distribution in a range of 75% of the average particle diameter to 125% of the average particle diameter, 80-120%, 85-115%, 86-114%, 87-113%, 88-112%, 89-111%, 90-110%, or preferably 95-105% of the average particle diameter.

In one embodiment, the nanocapsules are polydisperse with a coefficient of variation or relative standard deviation (ratio of the particle size standard deviation to the particle size mean) of more than 15%, 20%, or 30%. The polydisperse nanocapsules may have a particle diameter distribution in a range of 25% of the average particle diameter to 175% of the average particle diameter, 30-160%, or 50-150% of the average particle diameter.

An average diameter (e.g., average particle diameter) of the nanocapsule, as used herein, refers to the average linear distance measured from one point on the nanocapsule through the center of the nanocapsule to a point directly across from it. An average diameter of the nanocapsule is at least 100 nm, 110 nm, 120 nm, 130 nm, 140 nm, 150 nm, 200 nm, or 220 nm, and up to 250 nm, 300 nm, or 500 nm.

As used herein, the term "bioactive compound" refers to a pharmaceutical-grade compound found in both plant and animal products or may be synthetically produced. A bioactive compound is a compound that has an effect on a tissue/cell and/or a living organism (e.g., the bioactive compound may have an influence on health).

The bioactive compound may be a monophenol; a flavonoid, such as flavonol, a flavanone, a flavone, a flavan-3-ol, an anthocyanin, an anthocyanidin, an isoflavone, a dihydroflavonol, a chalcone, and a coumestan (e.g., coumestrol); a phenolic acid; a hydroxycinnamic acid; a lignan; a tyrosol ester; a stillbenoid; a hydrolysable tannin, such as punicalagin; a carotenoid, such as a carotene and a xanthophyll; a monoterpene, such as limonene and perillyl alcohol; a saponin; a lipid, such as a phytosterol, a tocopherol, and an omega-3,6,9 fatty acid; a diterpene such as a withbaferin; a triterpinoid; a betalain, such as a betacyanin and a betaxanthin (e.g., indicaxanthin and vulgaxantbin); a dithiolthione such as sulphoraphane; a thiosulphonate such as allyl methyl trisulfide and diallyl sulfide; an indole; and a glucosinolate.

Exemplary monophenols include, without limitation, apiole, carnosol, carvacrol, dillapiole, and rosemarinol. Exemplary phenolic acids include, without limitation, ellagic acid, gallic acid, salicylic acid, tannic acid, vanillin, capsaicin, curcumin, and plumbagin. Exemplary hydroxycinnamic acids include, without limitation, caffeic acid, chlorogenic acid, cinnamic acid, ferulic acid, and coumarin. Exemplary lignans (phytoestrogens) include, without limitation, silymarin, matairesinol, secoisolariciresinol, pinoresinol, at d lariciresinol. Exemplary tyrosol esters include, without limitation, tyrosol, hydroxytyrosol, oleocanthal, and oleuropein. Exemplary stilbenoids include, without limitation, resveratrol, pterostilbene, and piceatannol. Exemplary flavonoids (polyphenols) include, without limitation, flavonols, quercetin, gingerol, kaempferol, myricetin, rutin, and isorhaninetin. Exemplary flavanones include, without limitation, hesperidin, naringenin, silybin, and eriodictyol. Exemplary flavones include, without limitation, apigenin, tangeritin, and luteolin. Exemplary flavan-3-ols include, without limitation, catechins, gallocatechin, epicatechin, epigallocatechin, epigallocatechin gallate, epicatechin gallate, theaflavin, theaflavin gallate, theaflavin digallate, and thearubigins. Exemplary anthocyanins and anthocyanidins include, without limitation, pelargonidin, peonidin, cyanidin, delphinidin, malvidin, and petunidin. Exemplary isoflavones (phytoestrogens) include, without limitation, daidzein, genistein, equol, and glycitein. Exemplary carotenoids (tetraterpenoids) include, without limitation, carotenes (e.g., α-carotene, β-carotene, γ-carotene, δ-carotene, tocotrienols, tocopherols, lycopene, neurosporene, phytofluene, phytoene) and xanthophylls (e.g., canthaxanthin, cryptoxanthin, zeaxanthin, astaxanthin, lutein, rubixanthin). Exemplary phytosterols include, without limitation, campesterol, β-sitosterol, γ-sitosterol, and stigmasterol. Exemplary ω-3,6,9 fatty acids include, without limitation, linolenic acid, docosahexaenoic acid, eicosapentaenoic acid, linoleic acid, eicosadienoic acid, arachidonic acid, oleic acid, and erucic acid. Exemplary triterpenoids include, without limitation, oleanolic acid, ursolic acid, betulinic acid, moronic acid, curcurbitacins, and lupeol. Exemplary betacyanins include, without limitation, betanin, isobetanin, probetanin, and neobetanin. Exemplary indoles and glucosinolates include, without limitation, indole-3-carbinol, sulforaphone, 3,3'-diindolylmethane, sinigrin, allicin, alliin, allyl isothiocyanate, and piperine. In some embodiments, the bioactive compound is curcumin, green tea polyphenols, punicalagin, diindolylmethane, oltipraz, tocotrienol, tocopherol, plumbagin, cyanidin, delphinidin, lycopene, lupeol, curcurbitacin-B, withaferin indole-3-carbinol, genestein, resveratrol, co-enzyme Q-10, ellagic acid, petunidin, malvidin, peonidin, sulforaphane, fennel extract, and combinations thereof.

Preferably, the bioactive compound is diindolylmethane, ellagic acid, or both. In embodiments where both diindolylmethane and ellagic acid are present, a weight ratio between diindolylmethane and ellagic acid is 1:100 to 100:1, 1:50 to 50:1, 1:20 to 20:1, 1:10 to 10:1, 1:5 to 5:1, 1:3 to 3:1, 1:2 to 2:1, or about 1:1. Preferably, the weight ratio is about 2:1. A combination of diindolymethane and ellagic acid may produce a synergistic effect in treating cancer and/or reducing toxicity (e.g., nephrotoxicity) induced by cancer therapy, for example, see Table 1.

The bioactive compound may be extracted from plants or synthesized using methods known to those of skill in the art. A purity of the bioactive compound may be at least 80%, 85%, 90%, 95%, 99%, or 99.9%, based on a weight of the bioactive compound. The bioactive compound may be a pharmaceutically acceptable analog or a pharmaceutically acceptable derivative of a plant-derived compound, such as oltipraz, which is an analog of 1,2-dithiol-3-thione, a compound that is found in many cruciferous vegetables. The bioactive compound may be in a form of a pharmaceutically acceptable salt, a pharmaceutically acceptable solvate, or a pharmaceutically acceptable prodrug.

The term "pharmaceutically acceptable salt" refers to mineral or organic acid salts of basic groups, such as amines, and alkali or organic salts of acidic groups such as carboxylic acids and phenols. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like. The pharmaceutically acceptable salts of the present disclosure can be synthesized from the parent compound, which contains a basic or acidic moiety, by conventional chemical methods. Generally, such salts can be prepared by reacting the free acid or base forms of the bioactive compound with a stoichiometric amount of the appropriate base or acid in water or in an organic solvent, or in a mixture of the two; generally, non-aqueous media like ether, ethyl acetate, ethanol, isopropanol, or acetonitrile are preferred. Salts may be formed when an acidic proton present in the parent compound (e.g., a polyphenol) either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

In some embodiments, the pharmaceutically acceptable salt refers to the bioactive compound containing a counter-ion. As used herein, the term "counter-ion" refers to an anion, preferably a pharmaceutically acceptable anion that is associated with a positively charged parent compound (e.g., the nitrogen atoms in diindolylmethane may be protonated and become positively charged). Non-limiting examples of pharmaceutically acceptable counter-ions include halides, such as fluoride, chloride, bromide, iodide, nitrate, sulfate, phosphate, amide, methanesulfonate, ethanesulfonate, p-toluenesulfonate, salicylate, malate, maleate, succinate, tartrate, citrate, acetate, perchlorate, trifluoromethanesulfonate (triflate), acetylacetonate, hexafluorophosphate, and hexafluoroacetvlacetonate. In some embodiments, the counter-ion is a halide, preferably chloride.

As used herein, "analog" refers to a chemical compound that is structurally similar to a parent compound, but differs slightly in composition (e.g., one atom or functional group is different, added, or removed). The analog may or may not have different chemical or physical properties than the original compound and may or may not have improved biological and/or chemical activity. For example, the analog may be more hydrophilic or it may have altered reactivity as compared to the parent compound. The analog may mimic the chemical and/or biologically activity of the parent compound (i.e., it may have similar or identical activity), or, in some cases, may have increased or decreased activity. The analog may be a naturally or non-naturally occurring variant of the original compound. Other types of analogs include isomers (enantiomers, diastereomers, and the like) and other types of chiral variants of a compound, as well as structural isomers.

As used herein, "derivative" refers to a chemically or biologically modified version of a chemical compound that is structurally similar to a parent compound and (actually or theoretically) derivable from that parent compound. A "derivative" differs from an "analog" in that a parent compound may be the starting material to generate a "derivative", whereas the parent compound may not necessarily be used as the starting material to generate an "analog". A derivative may or may not have different chemical or physical properties of the parent compound. For example, the derivative may be more hydrophilic or it may have altered reactivity as compared to the parent compound. Derivatization (i.e., modification) may involve substitution of one or more moieties within the molecule (e.g., a change in functional group). The term "derivative" also includes conjugates, and prodrugs of a parent compound (i.e., chemically modified derivatives which can be converted into the original compound under physiological conditions).

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis (Harper, N. J. (1962). Drug Latentiation in Jucker, ed. Progress in Drug Research, 4:221-294; Morozowich et al. (1977). Application of Physical Organic Principles to Prodrug Design in E. B. Roche ed. Design of Biopharmaceutical Properties through Prodrugs and Analogs, APhA; Acad. Pharm. Sci.; E. B. Roche, ed. (1977). Bioreversible Carriers in Drug in Drug Design, Theory and Application, APhA; H. Bundgaard, ed. (1985) Design of Prodrugs, Elsevier; Wang et al. (1999) *Curr. Pharm. Design.* 5(4):265-287; Pauletti et al. (1997). *Adv. Drug. Delivery Rev.* 27:235-256; Mizen et al. (1998) *Pharm. Biotech.* 11:345-365; Gaignault et al. (1996) *Pract. Med. Chem.* 671-696; M. Asgharnejad (2000). Improving Oral Drug Transport Via Prodrugs, in G. L. Amidon, P. I. Lee and E. M. Topp. Eds., Transport Processes in Pharmaceutical Systems, Marcell Dekker, p. 185-218; Balant et al, (1990) *Eur. J. Drug Metab. Pharmacokinet.*, 15(2): 143-53; Balimane and Sinko (1999) *Adv. Drug Delivery Rev.*, 39(1-3): 183-209; Browne (1997) *Clin. Neuropharmacol.* 20(1): 1-12; Bundgaard (1979) *Arch. Pharm. Chem.* 86(1): 1-39; H. Bundgaard, ed. (1985) Design of Prodrugs, New York: Elsevier; Fleisher et al. (1996) *Adv. Drug Delivery Rev.* 19(2): 115-130; Fleisher et al. (1985) *Methods Enzymol.* 112: 360-81; Farquhar D, et al. (1983) *J. Pharm. Sci.*, 72(3): 324-325; Han, H. K. et al. (2000) *AAPS PharmSci.*, 2(1): E6; Sadzuka Y. (2000) *Curr. Drug Metab.*, 1(1):31-48; D. M. Lambert. (2000) *Eur. J. Pharm. Sci.*, 11 Suppl 2:S15-27—each incorporated herein by reference in its entirety). In some embodiments, "pharmaceutically acceptable prodrugs" refer to a compound that is metabolized, for example hydrolyzed or oxidized, in the host to form the pharmaceutical composition of the present disclosure. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound. An example, without limitation, of a prodrug would be a compound of the present invention, which is, administered as an ester, phosphate, amide; carbamate, or urea.

The term "solvate" means a physical association of a bioactive compound with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. Solvate encompasses both solution-phase and isolable solvates. Exemplary solvates include, but are not limited to, hydrates, ethanolates, methanolates, and isopropanolates. Methods of solvation are generally known in the art.

The term "biocompatible" refers to a compound/material/composition that is substantially non-toxic in the in vivo environment of its intended use, and that is not substantially rejected by the subjects physiological system (i.e., is non-antigenic). As will be recognized by those of ordinary skill in the art, the biocompatibility of a particular compound/material/composition can be gauged by its toxicity, infectivity, pyrogenicity, irritation potential, reactivity, hemolytic activity, carcinogenicity, and/or immunogenicity. When introduced into a majority of subjects, a biocompatible compound/material/composition will not cause an adverse, long-lived, or escalating biological reaction or response, and is distinguished from a mild, transient inflammation, which typically accompanies surgery or implantation of foreign objects into a living organism.

A biocompatible polymer may be synthetic, natural, or blends thereof. The nanocapsule may contain up to 90 wt %, 95 wt %, 99 wt %, 99.9 wt % of the biocompatible polymer, based on a total weight of the nanocapsule. The biocompatible polymer may form the shell of the nanocapsule which encapsulates the bioactive compound. The shell provides a physical barrier that isolates the encapsulated bioactive compound from external materials, such as those found in biological systems, and thus controls the permeability and stability of the nanocapsule, and release rates of the bioactive compound. A shell thickness may be from 5-249 nm, 10-150 nm, or 15-80 nm. A shell viscosity may be 3 mPa·s to 6 mPa·s or 4 mPa·s to 5 mPa·s at 25° C. and 1 atm. The bonding (ionic and covalent) between the polymers and stabilizers (e.g., PLGA-PEG, deoxycholic acid, polyvinyl alcohol, chitosan) and the viscosity of the shell may contribute to a release rate of the bioactive compound from the nanocapsule and may be changed (e.g., by varying the composition of the biocompatible polymer) based on a desired release rate of the bioactive compound. The viscosity may be measured by EPR or fluorescence spectroscopy. The bioactive compound may be released through the pores of the shell. The pores of the shell may have a diameter in a range of 0.01-2 run, 0.05-1 urn, or 0.1-0.5 nm. The shell may contain amphiphilic synthetic block copolymers which contain at least one block of hydrophobic polymer and at least one block of hydrophilic polymer described hereinafter. In these embodiments, the exterior of the shell may be hydrophobic or hydrophilic, depending on the type of block polymer near the exterior of the nanocapsule.

The nanocapsule may have a positive zeta potential in a range of +5 to +30 mV, +10 to +20 mV, or +15 to +20 mV. In some embodiments, the nanocapsule may have a negative zeta potential in a range of −30 to −5 mV, −30 to −10 mV, or −20 to −15 mV. Zeta potential is the measurement of an electrical potential of the exterior surface of a nanocapsule and depends on the composition of the biocompatible polymer. For example, a nanocapsule with a biocompatible polymer comprising chitosan may have a positive zeta potential as chitosan has a large positive zeta potential. A slight (more negative more positive) electrical potential of the exterior surface may prevent nanocapsules from aggregating by creating an electronic barrier (electrostatic repulsion) between nanocapsules. An absolute value of electrical potential or zeta potential directly correlates to the non-aggregating potential of the nanocapsule. Aggregation may result in an ineffective nanocapsule for delivering the encapsulated compounds (e.g., the bioactive compounds).

A weight ratio between chitosan to PLEA-PEG may be in a range of 1:10 to 10:1, 1:5 to 5:1, or 2:1 to 1:2. The preferred weight ratio of chitosan to PLGA-PEG of about 2:1 may result in a positive zeta potential (described above) where a slightly positive zeta potential would allow for long residence time in the gut for sustained oral delivery due to the mucoadhesive properties of chitosan.

The biocompatible polymer may be biodegradable or biostable. Biodegradable polymers degrade in vivo as a function of chemical composition, method of manufacture, and composition structure. Biostable polymers, on the other hand, remain intact in vivo for extended periods of time ranging from several weeks to more and include polymers such as ethylene-vinyl acetate copolymers, polyurethanes, polyacrylonitriles, and certain polyphosphazenes.

In some embodiments, the biocompatible polymer is biodegradable. To provide a biocompatible polymer that is biodegradable, both synthetic and natural polymers may be used. Synthetic polymers may be preferred due to a more uniform and reproducible degradation. Examples of synthetic biodegradable polymers include, but are not limited to, polyanhydrides; polyhydroxyacids such as polylactic acid/polylactide, polyglycolic acids and copolymers thereof (e.g., poly(lactic-co-glycolic acid)); polyesters; polyamides; polyorthoesters; polyvinyl alcohols; polyurethanes; polyesteramides; polydioxanones; polyacetals; polyketals; polycarbonates; polyorthocarbonate, polyhydroxybutyrates; polyhydroxyvalerates; polyalkylene oxalates; polyalkylene succinates; polymalic acid; polymaleic anhydride; poly(lactide-fumarate); poly(lactide-co-glycolide fumarate); certain polyphosphazenes; and copolymers thereof. Examples of naturally-occurring, biodegradable polymers include, but are not limited to, proteins and polysaccharides such as collagen, chitosan, hyaluronic acid, albumin, and gelatin.

In some embodiments, the biocompatible polymer may be a polyoxyl-8 dodecyl ether, a polyoxyl-12 dodecyl ether, a nonoxynol 10, a nonoxynol 30, a polysorbate (also known as TWEEN™, e.g., polysorbate 20, la polysorbate 40, a polysorbate 60, polysorbate 80), a cyclodextrin, a poloxamers (e.g., PLURONIC™), a polyethylene glycol, and combinations thereof.

The biocompatible polymer may be a block copolymer comprising a hydrophobic polymer block and a hydrophilic polymer block. Examples of hydrophilic polymers include, without limitation, polyethylene glycol and poly(2-methyloxazoline). Examples of hydrophobic polymers include, without limitation, polydimethylsiloxane, polylactide, and polymethyl methacrylate.

In preferred embodiments, the biocompatible polymer comprises poly(lactic-co-glycolic acid) and polyethylene glycol. An amount of polylactic-co-glycolic acid) may range from 0.1-99.9 wt %, 0.5-90 wt %, 1-85 wt %, 5-80 wt %, 10-75 wt %, 20-70 wt %, 30-60 wt %, or 45-50 wt %. An amount of polyethylene glycol may range from 0.1-99.9 wt %, 0.5-90 wt %, 1-85 wt %, 5-80 wt %, 10-75 wt %, 20-70 wt %, 30-60 wt %, or 45-50 wt %. A weight ratio of the polylactic-co-glycolic acid) to polyethylene glycol may be in a range of 1:100 to 100:1, 70:1 to 1:70, 40:1 to 1:40, 20:1 to 1:20, 10:1 to 1:10, 5:1 to 1:5, or 1:2 to 2:1. The presence of these polymers may result in a nanocapsule with a favorable release rate of the bioactive compound by using ionic or covalent bonding described herein.

The polylactic-co-glycolic acid) may be a polymerization product of glycolic acid and L-lactide, D-lactide, a mixture of D-lactide and L-lactide, or meso-lactide. A monomer ratio of lactide to glycolide in poly(lactic-co-glycolic acid) may be in a range of 1:99 to 99:1, 1:50 to 50:1, 1:20 to 20:1, 1:10 to 10:1, 1:5 to or about 1:1. In some embodiments, the polylactic-co-glycolic acid) is a polymerization product of polylactic acid and polyglycolic acid. In these embodiments, a weight ratio of polylactic acid to polyglycolic acid may be in a range of 65:35 to 75:25, 67:33 to 73:27, or 69:31 to 71:29.

In some embodiments, the biocompatible polymer is a copolymer of poly(lactic-co-glycolic acid) and polyethylene glycol. The copolymer may be a diblock or an alternating multiblock (e.g., a triblock) copolymer. The triblock copolymer may be PLEA-PEG-PLGA or PEG-PLGA-PEG. A number average molecular weight of the polyethylene glycol block may be at least 400 Da, 2 kDa, or 3 kDa and not more than 5 kDa, 6 kDa, or 7 kDa. A number average molecular weight of the polylactic-co-glycolic acid) block may be at least 4 kDa, 5 kDa, or 6 kDa and not more than 15 kDa, 20 kDa, or 25 kDa. A number average molecular weight ratio of polyethylene glycol block to the polylactic-co-glycolic acid) block may be 1:20 to 20:1, 1:10 to 10:1, 1:5 to 5:1, or about 1:1. A total number average molecular weight of the copolymer may be at least 3 kDa, 7 kDa. or 13 kDa and not more than 30 kDa, 31 kDa, or 32 kDa.

In some embodiments, the biocompatible polymer contains 1-50 wt %, 5-40 wt %, or 10-30 wt % of chitosan, a derivative thereof, or a combination thereof, based on a total weight of the biocompatible polymer. Chitosan is a polysaccharide copolymer of N-acetyl-D-glucosamine and D-glucosamine, obtained by the alkaline deacetylation of chitin obtained from crustaceans, such as shrimps, squids and crabs (Onishi H, Machida Y (1999) Biomaterials 20:175; Yanga J, Shibb I, Tzengc Y, Wang S (2000) Enzyme Microb Technol 26:406; and Khan T A, Peh K K, Chug H S (2002) J Pharm Sci 5:205, each incorporated herein by reference in their entirety). The chitosan may or may not be quaternized chitosan. Derivatives of chitosan, such as chitosan oligosaccharide lactate, trimethylchitosan, and glycol chitosan, which have a higher solubility in water than the unmodified chitosan may be preferred. The chitosan or derivative thereof in the nanocapsule may have a weight average molecular weight ranging from 1-10 kDa, preferably 2-8 kDa, more preferably 3-6 kDa. The weight average molecular weight may be measured by gel permeation chromatography. A degree of deacetylation of chitosan ranges from more than 40 wt %, 60 wt %, or 75 wt % relative to the total weight of chitosan. As used herein, the term "degree of deacetylation" refers to the percentage mass of D-glucosamine present in chitosan and can be determined by methods, such as titration and UV-vis spectrometry, which are known to those skilled in the art (Yuan et al. (2011) Materials 4:1399, incorporated herein by reference in its entirety).

In some embodiments, the biocompatible polymer is a copolymer such as PLGA-chitosan, PLGA-PEG-chitosan, PLGA-chitosan-PEG, and/or chitosan-PLGA-PEG. In these embodiments, chitosan may interact with the other polymer block by electrostatic (i ionic) interactions (e.g., the amine groups on chitosan are protonated by the carboxylic groups in PLGA) or by covalent bonds (e.g., using a coupling agent, such as EDC, to covalent bond the amine groups on chitosan with the carboxylic groups in PLGA). The copolymers containing chitosan may be prepared by methods known to those skilled in the art. FIGS. 8A, 8B, 9A, 9B, and 10A-10I describe embodiments of the disclosed nanocapsules in which the biocompatible polymer contains PLGA-PEG and chitosan.

Polymers with a low number average molecular weight (e.g., less than 5 kDa, 4 kDa, or 3 kDa) may be preferred because they degrade faster thereby increasing the release rate of the bioactive compound or other therapeutic agent. Preferably, the biocompatible polymer is not polycaprolactone because its degradation is slower than that of the polymers described above (e.g., polylactide and copolymers of PLGA and PEG).

In some embodiments, the nanocapsule contains polyvinyl alcohol in an amount not more than 5 wt %, 4 wt %, 2 wt %, or 0.5 wt %, based on a total weight of the nanocapsule. The polyvinyl alcohol may have a weight average molecular weight from 85 kDa to 100 kDa or 90 kDa to 95 kDa.

In some embodiments, the nanocapsule may contain a cryoprotectant that prevents the freezing of nanocapsule, or prevents damage to nanocapsule during freezing and/or freeze-drying. Exemplary cryoprotectants include, without limitation, mannitol, sucrose, trehalose, DMSO, glycols (e.g., alcohols containing at least two hydroxyl groups such as ethylene glycol, propylene glycol, and glycerol), and mixtures thereof. An amount of the cryoprotectant may be not more than 5 wt %, 4 wt %, 2 wt %, 1 wt %, or 0.5 wt %, based on a total weight of the nanocapsule.

Further, the nanocapsule may contain up to 10 wt %, 9 wt %, $ wt %, 7 wt %, 6 wt %, 5 wt %, 4 wt %, 3 wt %, 2 wt %, or 1 wt % of an anticancer agent, based on a total weight of the nanocapsule. The amounts of the bioactive compound and/or the anticancer agent may be adjusted to minimize the side effects of chemotherapy while maintaining the efficacy/ stability of the nanocapsule.

The anticancer agent is at least one of a mitotic inhibitor; an alkylating agent; an anti-metabolite; a cell cycle inhibitor;

an enzyme; a topoisomerase inhibitor such as CAMP-TOSAR (irinotecan); a biological response modifier; an anti-hormone; an antiangiogenic agent such as MMP-2, MMP-9 and COX-2 inhibitor; an anti-androgen; a platinum coordination complex (cisplatin, oxaliplatin, carboplatin); a substituted urea such as hydroxyurea; methylhydrazine derivative, e.g., procarbazine; an adrenocortical suppressant, e.g., mitotane, aminoglutethimide; a hormone and/or hormone antagonist such as the adrenocorticosteriods (e.g., prednisone), progestins hydroxyprogesterone caproate), an estrogen (e.g., diethylstilbestrol); an antiestrogen such as tamoxifen; androgen, e.g., testosterone propionate; and an aromatase inhibitor, such as anastrozole, and AROMASIN (exemestane).

Examples of alkylating agents include, without limitation, fluorouracil (5-FU) alone or in further combination with leukovorin; other pyrimidine analogs such as UFT, capecitabine, gemcitabine and cytarabine; the alkyl sulfonates, busulfan (used in the treatment of chronic granulocytic leukemia), improsulfan and piposulfan; aziridines, e.g., benzodepa, carboquone, meturedepa and uredepa; ethyleneimines and methylmelamines, e.g., altretamine, triethylenemelamine, triethylenephosphoramide, triethylenethiophosphoramide and trimethylolmelamine; and the nitrogen mustards, e.g., chlorambucil (used in the treatment of chronic lymphocytic leukemia, primary macroglobulinemia and non-Hodgkin's lymphoma), cyclophosphamide (used in the treatment of Hodgkin's disease, multiple myeloma, neuroblastoma, breast cancer, ovarian cancer, lung cancer, Wilm's tumor and rhabdomyosarcoma), estramustine, ifosfamide, novembrichin, prednimustine and uracil mustard (used in the treatment of primary thrombocytosis, non-Hodgkin's lymphoma, Hodgkin's disease and ovarian cancer); and triazines, e.g., dacarbazine (used in the treatment of soft tissue sarcoma).

Examples of antimetabolite anticancer agents include, without limitation, folic acid analogs, e.g., methotrexate (used in the treatment of acute lymphocytic leukemia, choriocarcinoma, mycosis fungoides, breast cancer, head and neck cancer and osteogenic sarcoma) and pteropterin; and the purine analogs such as mercaptopurine and thioguanine which find use in the treatment of acute granulocytic, acute lymphocytic and chronic granulocytic leukemias.

Examples of natural product-based anticancer agents that the above method can be carried out in combination with include, without limitation, the vinca alkaloids, e.g., vinblastine (used in the treatment of breast and testicular cancer), vincristine and vindesine; the epipodophyllotoxins, e.g., etoposide and teniposide, both of which are useful in the treatment of testicular cancer and Kaposi's sarcoma; the antibiotic anticancer agents, e.g., daunorubicin, doxorubicin, epirubicin, mitomycin (used to treat stomach, cervix, colon, breast, bladder and pancreatic cancer), dactinomycin, temozolomide, plicamycin, bleomycin (used in the treatment of skin, esophagus and genitourinary tract cancer); and the enzymatic anticancer agents such as L-asparaginase.

Examples of useful COX-II inhibitors include Vioxx, CELEBREX (celecoxib), valdecoxib, paracoxib, rofecoxib, and COX 189.

Some examples of MMP inhibitors useful are AG-3340, RO 32-3555, RS 13-0830, and compounds such as 3-[[4-(4-fluorophenoxy)-benzenesulfonyl]-(1-hydroxycarbamoyl-cyclopentyl)-amino]-propionic acid; 3-exo-3-[4-(4-fluoro-phenoxy)-benzenesulfonylamino]-8-oxa-bicyclo[3.2.1] octane-3-carboxylic acid hydroxyamide; (2R,3R) 1-[4-(2-chloro-4-fluoro-benzyloxy)-benzenesulfonyl]-3-hydroxy-3-methylpiperidine-2-carboxylic acid hydroxyamide; 4-[4-(4-fluorophenoxy)-benzenesulfonylamino]-tetrahydro-pyran-4-carboxylic acid hydroxyamide; 3-[[4-(4-fluoro-phenoxy) benzenesulfonyl]-(1-hydroxycarbamoyl-cyclobutyl)-amino]-propionic acid; 4-[4-(4-chloro-phenoxy) benzenesulfonylamino]-tetrahydro-pyran-4-carboxylic acid hydroxyamide; (R) 3-[4-(4-chloro-phenoxy)-benzenesulfonylamino]-tetrahydro-pyran-3-carboxylic acid hydroxyamide; (2R,3R) 1-[4-(4-fluoro-2-methylbenzyloxy)-benzenesulfonyl]-3-hydroxy-3-methyl-piperidine-2-carboxylic acid hydroxyamide; 3-[[(4-(4-(4-fluoro-phenoxy)-benzenesulfonyl]-hydroxycarbamoyl-1-methyl-ethyl)-amino]-propionic acid; 3-[[4-(4-fluoro-phenoxy)-benzenesulfonyl]-(4-hydroxycarbamoyl-tetrahydro-pyran-4-yl)-amino]-propionic acid; 3-exo-3-[4-(4-chloro-phenoxy)-benzenesulfonylamino]-8-oxa-bicyclo[3.2.1]octane-3-carboxylic acid hydroxyamide; 3-endo-3-[4-(4-fluorophenoxy)-benzenesulfonylamino]-8-oxa-bicyclo [3.2.1]octane-3-carboxylic acid hydroxy amide; and (R) 3-[4-(4-fluoro-phenoxy)-benzenesulfonylamino]-tetrahydro-furan-3-carboxylic acid hydroxyamide; and pharmaceutically acceptable salts and solvates of these compounds.

The nanocapsule may comprise other anticancer agents, including, but not limited to, agents capable of enhancing antitumor immune responses, such as CTLA4 (cytotoxic lymphocite antigen 4) antibodies, other agents capable of blocking CTLA4, trastuzumab, cetuximab, panituinumab, rituximab, bevacizumab, mapatumumab, conatumumab, and lexatumumab.

In some embodiments, the platinum-based anticancer agent is at least one of cisplatin, carboplatin, and oxaliplatin. The platinum-based anticancer agent may be useful for treating bladder cancer, ovarian cancer, and other types of cancers described herein.

In one embodiment, the anticancer agent is at least one of doxorubicin, paclitaxel, and docetaxel. These anticancer agents may be useful for treating breast cancer, bladder cancer, ovarian cancer, prostate cancer, and other types of cancers described herein.

In one embodiment, the anticancer agent is gemcitabine and/or 5-fluorouracil. These anticancer agents may be useful for treating pancreatic cancer, and other types of cancers described herein.

In one embodiment, the anticancer agent is temozolomide, which may be useful for treating glioblastoma and other types of brain cancers.

An aspect of the disclosure relates to a method of making the nanocapsule. The method steps may be carried out at a temperature in a range of 16-32>"C, 20-30° C., or 24-28° C. A stock solution of the biocompatible polymer may be prepared by dispersing the biocompatible polymer in an organic solvent. An amount of the biocompatible polymer may be 10-200 mg/ml, 30-150 mg/ml, or 50-100 mg/ml. A stock solution of the bioactive compound may be prepared by dissolving the bioactive compound in the same or different organic solvent. An amount of the bioactive compound may be 1-20 mg/ml, 3-15 mg/ml, or 5-10 mg/ml. A stock solution of the anticancer agent may be prepared by dissolving the anticancer agent in the same or different organic solvent. An amount of the anticancer agent may be 1-20 mg/ml, 3-15 mg/ml, or 5-10 mg/mi. The stock solutions of the biocompatible polymer and the bioactive compound, and optionally the stock solution of the anticancer agent, may be mixed by agitating the mixture by an agitator, a vortexer, a rotary shaker, a magnetic stirrer, a centrifugal mixer, or an overhead stirrer for 10-60 seconds, 20-50 seconds, or 30-40 seconds. In another embodiment, the mixture is left to stand (i.e. not stirred). In one embodiment, the mixture is sonicated in an ultrasonic bath or with an ultrasonic probe. A volume ratio between the biocompatible polymer stock solution and the bioactive compound stock solution may be between 10:1 to 1:10, 5:1 to 1:5, 2:1 to 1:2, or about 1:1. The resulting mixture may be mixed with a buffer in a volume ratio of 100:1 to 1:10, 50:1 to 1:5, 20:1 to 1:2, or 10:1 to 4:1 and then agitated for 10-60 seconds, 20-50 seconds, or 30-40 seconds with the methods described herein thereby obtaining a first emulsion. Preferably, the resulting mixture is mixed with the buffer by sonicating the emulsion more than once, or about 2-3 times and each sonication may last for 10-60 seconds, 20-50 seconds, or 30-40 seconds. A pH of the buffer may be 6-8, 6.3-7.6, or 6.8-7.2. The first emulsion may be, mixed with a solution containing an aqueous solution containing an emulsifier and then agitated with the methods described herein thereby obtaining a second emulsion, which is a water-in-oil-in-water emulsion. A volume ratio of the first emulsion to the aqueous solution may be 1:1 to 1:100, 1:2 to 1:20, or 1:5 to 1:10. The aqueous solution may contain up to 5% w/v, 4% w/v, 3% w/v, 2% w/v, 1% w/v, or 0.05% w/v of emulsifier, based on a total volume of the aqueous solution. The second emulsion may be mixed with another volume of the same aqueous solution and then agitated for 10-60 minutes, 20-50 minutes, or 30-40 minutes with the methods described herein. A volume of the second emulsion to the aqueous solution may be 1:1 to 1:100, 1:2 to 1:50, or 1:5 to 1:20. After the agitation, the organic solvent may be removed under a reduced pressure (e.g., 10-500 mbar, 50-300 mbar, or 100-200 mbar). The remaining solution may be dialyzed using a dialysis membrane (e.g., a membrane with a molecular cutoff weight of less than 20 kDa, 15 kDa, or 12 kDa) against water for 10-50 hours, 15-40 hours, or 20-30 hours thereby removing bioactive compounds which are not encapsulated. The dialyzed solution may be then lyophilized and stored.

Exemplary organic solvents include ethers (e.g. diethyl ether, dibutyl ether, tetrahydrofuran, 1,4-dioxane, tetrahydropyran, t-butyl methyl ether, cyclopentyl methyl ether, di-iso-propyl ether), alcohols (e.g., methanol, ethanol, trifluoroethan 1, n-propanol, i-propanol, n-butanol, i-butanol, t-butanol, n-pentanol, i-pentanol, 2-methyl-2-butanol, 2-trifluoromethyl-2-propanol, 2,3-dimethyl-2-butanol,3-pentanol, 3-methyl-2-pentanol, 2-methyl-3-pentanol, 2-methyl-2-pentano 2,3-di methyl-3-pentanol, 3-ethyl-3-ethanol, 2 methyl-2-hexanol, 3-hexanol, cyclopropylmethanol, cyclopropanol, cyclobutanol, cyclopentanol, cyclohexanol), aromatic solvents (e.g. benzene, o-xylene, m-xylene, p-xylene, and mixtures of xylenes, toluene, mesitylene, anisole, 1,2-dimethoxybenzene, trifluoromethylbenzene, fluorobenzene), hydrocarbons (e.g., cyclohexane, hexane, isooctane, n-pentane), glycol ethers (e.g. 1,2-dimethoxyethane, diglyme, triglyme), alkyl methyl sulfoxides dimethyl sulfoxide, decylmethyl sulfoxide, tetradecylmethyl sulfoxide), ketones (e.g., acetone, butanone), esters (e.g. ethyl acetate, propyl acetate), amides/lactams (e.g., dimethylformamide, dimethylacetamide, pyrrolidone, N-methyl-2-pyrrolidone, N-(2-hydroxyethyl) pyrrolidone), acetonitrile, propionitrile, butyronitrile, benzonitrile, ethylene carbonate, propylene carbonate, 1,3-dimethyl-3,4,5,6-tetrahydro-2(1H)-pyrimidinone, chlorinated solvents (e g., dichloromethane, chloroform, carbon tetrachloride, perchloroethylene (tetrachloroethylene), 1,1,2,2-tetrachloroethane, 1,1,2-trichloroethane, trichloroethylene, methyl chloroform (1,1,1-trichloroethane), 1,2,3-trichloropropane, ethylene dichloride, 1,2-dichloropropane (propylene dichloride), 1,2-dichloroethylene, 1,1-dichloroethane, chlorobenzene), and mixtures thereof. Preferably, the organic solvent is dichloromethane.

Exemplary buffer solutions include, without limitation, phosphate buffered saline (PBS), citrate buffer, maleate buffer, histidine buffer, bis-tris buffer, ethanolamine buffer, carbonate buffer, PIPES buffer, MOPSO buffer, imidazole buffer, BIS-TRIS propane buffer, BES buffer, MOPS buffer, HEPES buffer TES buffer, MOBS buffer, DIPSO buffer, TAPED buffer, and triethanolamine (TEA) buffer. Preferably, the buffer is PBS.

The aqueous solution containing the emulsifier may contain water which may be tap water, distilled water, doubly distilled water, deionized water, deionized distilled water, or combinations thereof. The water may be sterile. In one embodiment, the water may have a conductivity of less than 10 μS/cm, less than 5 μS/cm, or less than 1 μS/cm at 20-30° C.; and/or a resistivity greater than 0.1 MΩ·cm, greater than 1 MΩ·cm, greater than 5 MΩ·cm, or greater than 10 MΩ·cm at 20-30° C.; and/or a total solid concentration less than 5 mg/kg, less than 1 mg/kg, or less than 0.5 mg/kg; and/or a total organic carbon concentration less than 1000 μg/L, less than 200 μg/L, or less than 50 μg/L.

Exemplary emulsifiers include, without limitation, d-alpha tocopheryl polyethylene glycol 1000 succinate, polyvinyl alcohol, sodium alginate, type B gelatin, methylcellulose, sodium lauryl sulfate, sodium oleate, polysorbate 80, PLURONIC™, and mixtures thereof. Preferably, the emulsifier is polyvinyl alcohol. The emulsifier may interact with the bioactive compound to allow for a reduced interfacial tension between the bioactive compound and the biocompatible polymer in the process of making the nanocapsule. The emulsifier may allow for the bioactive compound to be encapsulated by the biocompatible polymer. In some embodiments, the emulsifier may also stabilize the membrane thereby resulting in a slow release rate of the bioactive compound from the nanocapsule.

An aspect of the disclosure relates to a pharmaceutical composition comprising the nanocapsule and at least one pharmaceutically acceptable carrier/excipient. The term "composition," as used herein, refers to two or more chemical entities that are mixed together to comprise a homogenous or heterogeneous solid, liquid, or gas.

The pharmaceutical composition may contain up to 10 wt %, 20 wt %, 30 wt %, 40 wt %, 50 wt %, 60 wt %, 70 wt %, 80 wt %, 90 wt %, 95 wt %, 99 wt %, or 100 wt % of the nanocapsule, based on a total weight of the composition. The pharmaceutical composition may also contain up to 10 wt %, 20 wt %, 30 wt %, 40 wt %, 50 wt %, 60 wt %, 70 wt %, 80 wt %, 90 wt %, 95 wt %, or 99 wt % of an anticancer agent described above, based on a total weight of the composition.

As used herein, a "pharmaceutically acceptable carrier" refers to a carrier or diluent that does not cause significant irritation to an organism, does not abrogate the biological activity and properties of the administered nanocapsule, and/or does not interact in a deleterious manner with the nanocapsule or other components of the pharmaceutical composition in which it is contained. The term "carrier" encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005, which is incorporated herein by reference in its entirety. Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.).

An "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

In some embodiments, the pharmaceutically acceptable carrier and/or excipient may be an organic solvent, a synthetic polymer, a fatty acid, a synthetic fatty ester, a vegetable oil, and a surfactant.

Exemplary fatty acids include, without limitation, an omega-3 fatty acid (e.g., linolenic acid, docosahexaenoic acid, eicosapentaenoic acid) and an omega-6 fatty acid (e.g., linoleic acid, eicosadienoic acid, arachidonic acid). Other fatty acids, such as oleic acid, palmitoleic acid, palmitic acid, stearic acid, and myristic acid, may be included.

Exemplary vegetable oils include, without limitation, avocado oil, olive oil, palm oil, coconut oil, rapeseed oil, soybean oil, corn oil, sunflower oil, cottonseed oil, and peanut oil, grape seed oil, hazelnut oil, linseed oil, rice bran oil, safflower oil, sesame oil, brazil nut oil, carapa oil, passion fruit oil, and cocoa butter.

Exemplary synthetic fatty esters include, without limitation, methyl, ethyl, isopropyl and butyl esters of fatty acids (e.g., isopropyl palmitate, glyceryl stearate, ethyl oleate, isopropyl myristate, isopropyl isostearate, diisopropyl sebacate, ethyl stearate, di-n-butyl adipate, dipropylene glycol pelargonate), $C_{12}$-$C_{16}$ fatty alcohol lactates (e.g., cetyl lactate and lauryl lactate), propylene dipelargonate, 2-ethylhexyl isononoate, 2-ethylbexyl stearate, isopropyl lanolate, 2-ethylhexyl salicylate, cetyl myristate, oleyl myristate, oleyl stearate, oleyl oleate, hexyl laurate, isohexyl laurate, propylene glycol fatty ester, and polyoxyethylene sorbitan fatty ester. As used herein, the term "propylene glycol fatty ester" refers to an monoether or diester, or mixtures thereof, formed between propylene glycol or polypropylene glycol and a fatty acid. The term "polyoxyethylene sorbitan fatty ester" denotes oleate esters of sorbitol and its anhydrides, typically copolymerized with ethylene oxide. A particular polyoxyethylene sorbitan fatty ester is polyoxyethylene 20 sorbitan monooleate also known as polysorbate 80 or Tween 80 (T80).

Surfactants may act as detergents, wetting agents, emulsifiers, foaming agents, and dispersants. Surfactants that can be present in the disclosed compositions include anionic surfactants, amphoteric surfactants, cationic surfactants, zwitterionic surfactants, non-ionic surfactants, and combinations thereof. Surfactants suitable for use in the present invention may include TWEEN®, polyethylene glycol, PLURONICS™ potassium laurate, sodium octane sulfonate, sodium decane sulfonate, sodium dodecane sulfonate, sodium lauryl sulfate, docusate sodium, decyltrimethylammonium bromide, dodecyltrimethylammonium bromide, tetradecyltrimethylammonium bromide, tetradecyltrimethyl-ammonium chloride, dodecylammonium chloride, polyoxyl-8 dodecyl ether, polyoxyl-12 dodecyl ether, nonoxynol 10, nonoxynol 30, and polysorbates such as polysorbate 20, polysorbate 40, polysorbate 60, or polysorbate 80.

One purpose of a pharmaceutical composition is to facilitate administration of the nanocapsule to a subject. Pharmaceutical compositions of the present invention may be manufactured by processes well known in the art, e.g., by means of conventional mixing, dissolving, granulating, dragee-making, levigating, emulsifying, encapsulating, entrapping or lyophilizing processes. Depending on the intended mode of administration (oral, parenteral, or topical), the composition can be in the form of solid, semi-solid or liquid dosage forms, such as tablets, suppositories, pills, capsules, powders, liquids, or suspensions, preferably in unit dosage form suitable for single administration of a precise dosage.

Solid dosage forms for oral administration can include capsules, tablets, pills, powders, and granules. In such solid dosage forms, the nanocapsule is ordinarily combined with one or more adjuvants appropriate to the indicated route of administration. When administered orally, the nanocapsule may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering ingredients such as sodium citrate, magnesium or calcium carbonate or bicarbonate. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting ingredients, emulsifying and suspending ingredients, and sweetening, flavoring, and perfuming ingredients.

For therapeutic purposes, formulations for parenteral administration can be in the form of aqueous or non-aqueous isotonic sterile injection solutions or suspensions. The term "parenteral", as used herein, includes intravenous, intravesical, intraperitoneal, subcutaneous, intramuscular, intralesional, intracranial, intrapulmonal, intracardial, intrasternal, and sublingual injections, or infusion techniques. These solutions and suspensions can be prepared from sterile powders or granules having one or more of the carriers or diluents mentioned for use in the formulations for oral administration. The nanocapsule may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Injectable preparations, for example, sterile injectable aqueous or oleaginous suspensions can be formulated according to the known art using suitable dispersing or wetting ingredients and suspending ingredients. The sterile injectable preparation can also be a sterile injectable solution or suspension in a non-toxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids, such as oleic acid, find use in the preparation of injectables. Dimethyl acetamide, surfactants including ionic and non-ionic detergents, polyethylene glycols can be used. Mixtures of solvents and wetting ingredients such as those discussed above are also useful.

Suppositories for rectal administration can be prepared by mixing the nanocapsule with a suitable non-irritating excipient, such as cocoa butter, synthetic mono-, di-, or triglycerides, fatty acids, and polyethylene glycols that are solid at ordinary temperatures but liquid at the rectal temperature and will therefore melt in the rectum and release the drug.

Topical administration can also involve the use of transdermal administration such as transdermal patches or iontophoresis devices. Formulation of drugs is discussed in, for example, Hoover, John E., Remington's Pharmaceutical Sciences, Mack Publishing Co., Easton, Pa., 1975. Another example of includes Liberman, H. A. and Lachman, Eds., Pharmaceutical Dosage Forms, Marcel Decker, New York, N.Y., 1980, which is incorporated herein by reference in its entirety).

The nanocapsule may have various release rates (e.g. controlled release or immediate release). Immediate release refers to the release of the bioactive compound substantially immediately upon administration. In another embodiment, immediate release occurs when there is dissolution of a bioactive compound within 1-20 minutes after administration. Dissolution can be of all or less than all (e.g. about 70%, about 75%, about 80%, about 85%, about 90%, about 91%, about 92%, about 93%, about 94%, about 95%, about 96%, about 97%, about 98%, about 99%, about 99.5%, 99.9%, or 99.99%) of the bioactive compound. In another embodiment, immediate release results in complete or less than complete dissolution within about 1 hour following administration. Dissolution can be in a subject's stomach and/or intestine. In one embodiment, immediate release results in dissolution of a bioactive compound within 1-20 minutes after entering the stomach. For example, dissolution of 100% of a bioactive compound can occur in the prescribed time. In another embodiment, immediate release results in complete or less than complete dissolution within about 1 hour following rectal administration. In some embodiments, immediate release is through inhalation, such that dissolution occurs in a subject's lungs.

Controlled-release, or sustained-release, refers to the release of a bioactive compound from a nanocapsule or dosage form in which the bioactive compound is released over an extended period of time. In one embodiment, controlled-release results in dissolution of a bioactive compound within 20-180 minutes after entering the stomach. In another embodiment, controlled-release occurs when there is dissolution of a bioactive compound within 20-180 minutes after being swallowed. In another embodiment, controlled-release occurs when there is dissolution of a bioactive compound within 20-180 minutes after entering the intestine. In another embodiment, controlled-release results in substantially complete dissolution after at least 1 hour following administration. In another embodiment, controlled-release results in substantially complete dissolution after at least 1 hour following oral administration. In another embodiment, controlled-release results in substantially complete dissolution after at least 1 hour following rectal administration.

Another aspect of the disclosure relates to a method for treating cancer. The method includes administrating an effective amount of a bioactive compound encapsulated by a biocompatible polymer, and an effective amount of an anticancer agent to a subject in need thereof. In most embodiments, the method disclosed herein does not cause neuropathy and/or cardiotoxicity in the subject. The bioactive compound may be at least one bioactive compound described above. The anticancer agent may or may not be encapsulated by the biocompatible polymer. In preferred embodiments, the bioactive compound is diindolylmethane, ellagic acid, or both (the ratio diindolylmethane:ellagic acid is described above), and/or the anticancer agent is cisplatin or doxorubicin.

In some embodiments, the combination of diindolylmethane, ellagic acid, and cisplatin may exhibit synergy in treating cancer without causing any peripheral neuropathy when compared to a subject administered with cisplatin only. Symptoms of cancer therapy—induced peripheral neuropathy include, without limitation, sensory impairment, sensorimotor neuropathy, pure motor neuropathy, distal axonopathy, paraesthesia, allodynia, and hyperalgesia. Peripheral neuropathy may be diagnosed and/or quantified with methods such as quantitative sensory testing (QST), nerve conduction tests, laser-Doppler-imager (UN) flare, and biopsy. The subject treated with cisplatin only may have: (1) a neuropathy disability score (on a scale of 0 to 10) of at least 4, at least 5, or at least 6, and up to 10; (2) a vibration perception threshold of at least 12 V, at least 15 V, or at least 18 V, and up to 20 V, 25 V, or 30V; and/or (3) a LDI flare area of not more than 3 cm$^2$, 4 cm$^2$, or 5 cm$^2$. The subject treated with the combination of cisplatin, diindolylmethane, and ellagic acid may have: (1) a neuropathy disability score (on a scale of 0 to 10) of not more than 1; (2) a vibration perception threshold of at least 5 V, at least 6 V, or at least 7 V, and up to 8 V, 9 V, or 10V; and/or (3) a LDI flare area of at least 5 cm$^2$, 6 cm$^2$, or 7 cm$^2$, and up to 8 cm$^2$, 9 cm$^2$, or 10 cm$^2$.

In some embodiments, the combination of diindolylmethane, ellagic acid, and cisplatin may exhibit synergy in treating cancer without causing any cardiotoxicity when compared to subjects administered with doxorubicin only. Cancer therapy-induced cardiotoxicity may be defined as one or more of the following: (1) reduction of left ventricular ejection fraction (LVEF), either global or specific in the interventricular septum; (2) symptoms or signs associated with heart failure (HF); and (3) reduction in LVEF from baseline by at least 5%, 10%, 20%, 30%, 40%, or 55% in the presence of signs or symptoms of HF, or a reduction in LVEF by at least 10%, 15%, or 20%, and up to 30%, 40%, or 55% without signs or symptoms of HF. Cardiac dysfunction associated with chemotherapy may be acute, subacute, or chronic. Cardiotoxicity may be diagnosed and/or quantified by methods such as radionuclide ventriculography (RVG), positron emission tomography (PET) and cardiac magnetic resonance (CMR), speckle tracking imaging, and echocardiography. Cardiotoxicity may also be monitored by quantifying biomarkers such as troponin, troponin I, cardiac natriuretic peptides, and myeloperoxidase. For example, the levels of troponin T and/or troponin I in a subject treated with doxorubicin only may be increased by at least 10%, 20%, or 30% compared to the respective troponin levels in a subject treated with a combination of doxorubicin, diindolylmethane, and ellagic acid. Cardiac troponin T (cTnT)

may show the greatest ability to detect myocardial damage assessed by cardiac histological changes in subjects. The myocardial damage may be reversed when the subject is treated with nanocapsules containing DIM, EA, and doxorubicin. A level of troponin I in a subject without cardiotoxicity may be less than 10 µg/L, 9 µg/L, or 8 µg/L, and at least 4 µg/L, 5 µg/L, and 6 µg/L. A level of troponin T in a subject without cardiotoxicity may be 0-0.1 µg/L, 0.01-0.07 µg/L, or 0.03-0.06 µg/L. The methods for determining the levels of the biomarkers are described hereinafter.

The effective amount of the bioactive compound may be in a range of 0.1-100 mg/kg, body weight of the subject, 1-100 mg/kg, 3-50 mg/kg, or 5-30 mg/kg. The effective amount of the anticancer agent may be in a range of 1-100 mg/kg body weight of the subject, 5-60 mg/kg, or 10-30 mg/kg. The bioactive compound may be administered in the form of the pharmaceutical composition described above. The anticancer agent may be present in the pharmaceutical composition and may or may not be encapsulated by the nanocapsule. In some embodiments, the administering of the bioactive compound and the anticancer agent may be staggered. For example, a time interval between the administration of the bioactive compound and the administration of the anticancer agent may be 1-5 minutes, 1-30 minutes, 30 minutes to 60 minutes, 1 hour, 1-2 hours, or 2-6 hours.

The administering of the bioactive compound and the anticancer agent may last for at least 2 weeks, 5 weeks, 10 weeks, or 20 weeks. The frequency of administering may be 1-20 times, 3-10 times, or 6-8 times per week.

In some embodiments, the quantification of the biomarker related to peripheral neuropathy/cardiotoxicity and/or the diagnosis of peripheral neuropathy may be performed before and/or after the administration of the encapsulated bioactive compound and anticancer agent. In some embodiments, the peripheral neuropathy/cardiotoxicity biomarkers are measured/detected after the administering of each dose of the bioactive compound. For example, the measurement may be 1-5 minutes, 1-30 minutes, 30-60 minutes, 1-2 hours, 2-12 hours, 12-24 hours, 1-2 days, 1-15 weeks, 15-20 weeks, 20-30 weeks, 30-40 weeks, 40-50 weeks, 1 year, 2 years, or any period of time in between after the administration.

When the concentration of the peripheral neuropathy/cardiotoxicity biomarker is maintained and/or peripheral neuropathy is not present, the effective amount of the bioactive compound is kept the same. When there are indications of peripheral neuropathy/cardiotoxicity (e.g., the concentration of the peripheral neuropathy/cardiotoxicity biomarker increased/decrease and/or LVEF is decreased), the effective amount of the bioactive compound may be increased by at least 5%, at least 10%, or at least 30%, up to 50%, up to 60%, or up to 80% of an initial effective amount. The increased effective amount may be in a range of 1.05-1,800 mg/kg, preferably 15-1.400 mg/kg, more preferably 25-909 mg/kg.

The cancer may be lung cancer, stomach cancer, colon cancer, liver cancer, ovarian cancer, kidney cancer, breast cancer, prostate cancer, uterus cancer, melanoma, esophageal cancer, brain cancer, pancreatic cancer, and combinations thereof. In preferred embodiments, the cancer is pancreatic cancer, colon cancer, glioma, and/or breast cancer. In some embodiments, the neoplastic activity of the tumor or cancer cells may be localized or initiated in one or more of the following: blood, bladder, cervix, rectum, intestine, spleen, head, neck, testicle, bone (including bone marrow), thyroid gland, and central nervous system.

In treating certain cancers, the best approach is a combination of surgery, radiotherapy, and/or chemotherapy. Therefore, in at least one embodiment, the method further includes subjecting the subject to radiotherapy and/or surgery. The radiotherapy and/or surgery may be before or after the anticancer agent is administered.

As used herein, the terms "treat". "treatment", and "treating" the context of the administration of a therapy to a subject in need thereof refer to the reduction or inhibition of the progression and/or duration of a disease (e.g., cancer and/or toxicity resulting from cancer therapy), the reduction or amelioration of the severity of the disease, and/or the amelioration of one or more symptoms thereof resulting from the administration of one or more therapies. "Treating" or "treatment" of the disease includes preventing the disease from occurring in a subject that may be predisposed to the disease but does not yet experience or exhibit symptoms of the disease (prophylactic treatment), inhibiting the disease (slowing or arresting its development), ameliorating the disease, providing relief from the symptoms or side-effects of the disease (including palliative treatment), and relieving the disease (causing regression of the disease). With regard to the disease, these terms simply mean that one or more of the symptoms of the disease will be reduced. Such terms may refer to one, two, three, or more results following the administration of one, two, three, or more therapies: (1) a stabilization, reduction (e.g. by more than 10%, 20%, 30%, 40%, 50%, preferably by more than 60% of the population of cancer cells and/or tumor size before administration), or elimination of the cancer cells, (2) inhibiting cancerous cell division and/or cancerous cell proliferation, (3) relieving to some extent (or, preferably, eliminating) one or more symptoms associated with a pathology related to or caused in part by unregulated or aberrant cellular division, (4) an increase in disease-free, relapse-free, progression-free, and/or overall survival, duration, or rate, (5) a decrease in hospitalization rate, (6) a decrease in hospitalization length, (7) eradication, removal, or control of primary, regional and/or metastatic cancer, (8) a stabilization or reduction (e.g. by at least 10%, 20%, 30%, 40%, 50%, 60%, 70%, preferably at least 80% relative to the initial growth rate) in the growth of a tumor or neoplasm, (9) an impairment in the formation of a tumor, (10) a reduction in mortality, (11) an increase in the response rate, the durability of response, or number of patients who respond or are in remission, (12) the size of the tumor is maintained and does not increase or increases by less than 10%, preferably less than 5%, preferably less than 4%, preferably less than 2%, (13) a decrease in the need for surgery (e.g. colectomy, mastectomy), and (14) preventing or reducing (e.g. by more than 10%, more than 30%, preferably by more than 60% of the population of metastasized cancer cells before administration) the metastasis of cancer cells.

In regard to peripheral neuropathy, "treat" and "treating" refer to one or more results following the administration of the bioactive compound alone or with the anticancer agent: (1) a neuropathy disability score (on a scale of 0 to 10) of not more than 1; (2) a vibration perception threshold of at least 5 V, at least 6 V, or at least 7 V. and up to 8 V, 9 V. or 10V, and/or (3) a LDI flare area of at least than 5 cm$^2$, 6 cm$^2$, or 7 cm$^2$, and up, to 8 cm$^2$, 9 cm$^2$, or 10 cm$^2$.

In regard to cardiotoxicity, "treat" and "treating" refer to one or more results following the administration of the bioactive compound alone or with the anticancer agent: (1) the left ventricular ejection fraction (LVEF), either global or specific in the interventricular septum, is more than 95%, 98%, or 99% of the LVEF in a normal, healthy subject; and/or (2) no symptoms or signs associated with heart failure (HF).

In regard to nephrotoxicity, "treat" and "treating" refer to one or more results following the administration of the bioactive compound alone or with the anticancer agent: (1) the level of serum creatinine in the subject is in a range of 0.4-1.3 mg/dL, 0.5-1.2 mg/dL, or 0.6-1.1 mg/dL; (2) the level of blood urea nitrogen in the subject is in a range of 5-20 mg/dL, 6-18 mg/dL, or 10-15 mg/dl; and (3) a NF-κB level not more than 1%, 2%, 3%, 4%, or 5% of a NF-κB level in a normal, healthy subject.

The nanocapsule may be administered in a single dose or multiple individual divided doses. In some embodiments, the nanocapsule is administered at various dosages (e.g. a first dose with an effective amount of 50 mg/kg and a second dose with an effective amount of 10 mg/kg). In some embodiments, the interval of time between the administration of the nanocapsule and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months, 5 months, 6 months, 7 months, S months, 9 months, 10 months, 11 months, 12 months, 1 year, 2 years, or any period of time in between. Preferably, the composition is administered once daily for at least 2 days, 5 days, 6 days, or 7 days. In certain embodiments, the nanocapsule and one or more additional therapies are administered less than 1 day, 1 week, 2 weeks, 3 weeks, 4 weeks, one month, 2 months, 3 months, 6 months, 1 year, 2 years, or 5 years apart.

The terms "administer", "administering", "administration", and the like, as used herein, refer to the methods that may be used to enable delivery of the bioactive compound and the anticancer agent and/or the nanocapsule containing both compounds to the desired site of biological action. Routes or modes of administration are as set forth herein. These methods include, but are not limited to, oral routes, intraduodenal routes, parenteral injection (including intravenous, subcutaneous, intraperitoneal, intramuscular, intravascular, or infusion), topical and rectal administration. Those of ordinary skill in the art are familiar with administration techniques that can be employed with the nanocapsule and methods described herein. In preferred embodiments, the nanocapsule and/or the composition described herein are administered orally.

The terms "patient", "subject", and "individual" are used interchangeably. As used herein, they refer to individuals suffering from a disease and encompass mammals. None of the terms require that the individual be under the care and/or supervision of a medical professional. Mammals are any member of the mammalian class, including but are not limited to humans, non-human primates, such as chimpanzees, and other apes and monkey species, farm animals, such as cattle, horses, sheep, goats, swine, domestic animals, such as rabbits, dogs, and cats, laboratory animals including rodents, such as rats, mice and guinea pigs, and the like. In preferred embodiments, the subject is a human.

A subject in need of treatment includes a subject already with the disease, a subject which does not yet experience or exhibit symptoms of the disease, and a subject predisposed to the disease. In preferred embodiments, the subject is a person who is predisposed to cancer, e.g. a person with a family history of cancer. Women who have (i) certain inherited genes (e.g. mutated BRCA1 and/or mutated BRCA2). (ii) been taking estrogen alone (without progesterone) after menopause for many years (at least 5, at least 7, or at least 10), and/or (iii) been taking fertility drug clomiphene citrate, are at a higher risk of contracting ovarian cancer. White women or a person with (i) certain inherited genes (e.g. mutated BRCA1, BRCA2, ATM, TP53, CHEK2, PTEN, CDH1, STK11, and PALB2) (ii) radiation to one's chest, and/or (iii) exposure to diethylstilbestrol (DES), are at a higher risk of contracting breast cancer. African Americans, Jews of Eastern European descent, or a person with: (i) a personal history of colorectal polyps and/or inflammatory bowel disease, (ii) a family history of adenomatous polyps, (iii) an inherited syndrome (Lynch syndrome, Turcot syndrome, Peutz-Jeghers syndrome, MUTYH-associated polyposis), and/or (iv) type 2 diabetes, are at a higher risk of contracting colon cancer. The subject may be at a higher risk of developing glioma when the subject or a family member has Li-Fraumeni syndrome, neurofibromatosis, nevoid basal cell carcinoma syndrome, tuberous sclerosis, Turcot syndrome, and/or von Hippel-Lindau disease. The subject may be at a higher risk of developing pancreatic cancer when the subject is: (i) older than 45, (ii) a male, (iii) black or of Ashkenazi Jewish heritage, (iv) obese, (v) taking part in unhealthy habits such as smoking and heavy thinking, and/or (vi) diabetic. In some embodiments, the subject may be at a higher risk of developing pancreatic cancer when a family member of the subject has inherited one or more of the following conditions: hereditary pancreatitis, Peutz-Jeghers syndrome, familial malignant melanoma and pancreatic cancer, hereditary breast and ovarian cancer syndrome, and Lynch syndrome. In some embodiments, the subject may be at a higher risk of developing pancreatic cancer when the subject has one or more of the following conditions: Li-Fraumeni syndrome, familial adenomatous polyposis, chronic pancreatitis, and Hepatitis B.

In another embodiment, the subject refers to a cancer patient who has been previously administered/treated with cisplatin and have cisplatin resistance (for example in the form of high ERCC1 mRNA levels, overexpression of HER-2/neu, activation of the PI3-KAkt pathway, loss of p53 function, and/or overexpression of antiapoptotic bcl-2). In these embodiments, the subject may be treated with doxorubicin or any anticancer agent which is not cisplatin.

The methods for treating cancer and other proliferative disorders described herein inhibit, remove, eradicate, reduce, regress, diminish, arrest or stabilize a cancerous tumor, including at least one of the tumor growth, tumor cell viability, tumor cell division and proliferation, tumor metabolism, blood flow to the tumor and metastasis of the tumor. In some embodiments, the size of a tumor, whether by volume, weight or diameter, is reduced after the treatment by at least 5%, 10%, 15%, 20%, 25%, 30%, 40%, 50%, 60%, 70%, 75%, 80%, 85%, 90%, 95%, or 99%, relative to the tumor size before treatment. In other embodiments, the size of a tumor after treatment does not reduce but is maintained the same as the tumor size before treatment. Methods of assessing tumor size include but are not limited to CT scan, MRI, DCE-MRI and PET scan.

As used herein, the terms "therapies" and "therapy" can refer to any method, composition, and/or bioactive compound that can be used in the treatment and/or management of the disease or one or more symptoms thereof. In some embodiments, the method for treating the disease involves the administration of a unit dosage or a therapeutically effective amount of the bioactive compound/anticancer agent to a subject in need thereof.

The terms "effective amount", "therapeutically effective amount", or "pharmaceutically effective amount" refer to that amount of the bioactive compound/anticancer agent being administered which will relieve to some extent one or more of the symptoms of the disease being treated. The result can be reduction and/or alleviation of the signs, symptoms, or causes of a disease, or any other desired alteration of a biological system. For example, an "effective amount" for therapeutic uses is the amount of the bioactive compound/anticancer agent as disclosed herein required to provide a clinically significant decrease in a disease. An appropriate "effective amount" may differ from one individual to another. An appropriate "effective amount" in any individual case may be determined using techniques, such as a dose escalation study.

The dosage and treatment duration are dependent on factors, such as bioavailability of a drug, administration mode, toxicity of a drug, gender, age, lifestyle, body weight, the use of other drugs and dietary supplements, the disease stage, tolerance and resistance of the body to the administered drug, etc., and then determined and adjusted accordingly.

In most embodiments, the method further comprises measuring a concentration of a cancer biomarker and/or detecting a mutation (e.g., methylation) in a cancer biomarker before and/or after the nanocapsule is administered. As used herein, the term "biomarker" refers to a characteristic that is objectively measured and evaluated as an indicator of normal biological processes, pathogenic processes or pharmacological responses to a therapeutic intervention. Generic cancer biomarkers include circulating tumor DNA (ctDNA) and circulating tumor cells (CTC). Exemplary cancer biomarkers for breast cancer include, without limitation, BRCA1, BRCA2, HER-2, estrogen receptor, progesterone receptor, cancer antigen 15-3, cancer antigen 27.29, carcinoembryonic antigen, Ki67, cyclin D1, cyclin E, and ERβ. Specifically, potentially predictive cancer biomarkers include, without limitation, mutations in genes BRCA1 and BRCA2 for breast cancer. Cancer biomarkers may be useful in determining the aggressiveness of an identified cancer as well as its likelihood of responding to the treatment. Examples of such prognostic cancer biomarkers include, without limitation, elevated expression of estrogen receptor (ER) and/or progesterone receptor (PR), which are associated with better overall survival in patients with breast cancer.

Exemplary cancer biomarkers for pancreatic cancer include, without limitation, CA19-9, KRAS, CD1D, KCNK12, CLEC11A, NDRG4, IKZF1, PKRCB, ppENK, cyclin D2, spare-7, osteonectin, and TSLC1.

Exemplary cancer biomarkers for colon cancer include, without limitation, BRAT, KRAS, epidermal growth factor receptor (EGFR), and vimentin.

Exemplary cancer biomarkers for glioma include, without limitation, O(6)-methylguanine-DNA-methyltransferase (MGMT) promoter, EGFR, epidermal growth factor, latrophilin, 7 transmembrane domain-containing protein 1 on chromosome 1 (ELTD1), vascular endothelial growth factor (VEGF), tumor suppressor protein p53, phosphatase and tensin homolog (PTEN), p16INK4a gene, cytochrome c oxidase (CcO), and telomerase messenger expression (hTERT messenger ribonucleic acid).

The mutation in the cancer biomarker may be detected with a polymerase chain reaction (PCR) assay, DNA microarray, multiplex ligation-dependent probe amplification (MLPA), single strand conformational polymorphism (SSCP), denaturing gradient gel electrophoresis (DGGE), heteroduplex analysis, and restriction fragment length polymorphism (RFLP). The procedures to detect the mutation are well-known to those of ordinary skill in the art.

The concentration of the biomarkers described herein may be measured with an assay, for example an antibody-based method (e.g. an ELISA). As used herein, the term "antibody-based method" refers to any method with the use of an antibody including, but not limited to, enzyme-linked immunosorbent assay (ELISA), Western blotting, immunoprecipitation (IP), enzyme linked immunospot (ELISPOT), immunostaining, immunohistochemistry, immunocytochemistry, affinity chromatography, and the like.

Preferably, an ELISA is used. The term "ELISA" refers to a method of detecting the presence and concentration of a biomarker in a sample. There are several variants of ELISA, including, but not limited to, sandwich ELISA, competitive ELISA, indirect ELISA, ELISA reverse, and the like. The ELISA assay may be a singleplex assay or a multiplex assay, which refers to a type of assay that simultaneously measures multiple analytes in a single run/cycle of the assay. Preferably, a sandwich ELISA is used.

The protocol for measuring the concentration of the biomarker and/or detecting the mutation in the biomarker is known to those of ordinary skill, for example by performing the steps outlined in the commercially available assay kit sold by Sigma-Aldrich, Thermo Fisher Scientific, R & D Systems, ZeptoMetrix Inc., Cayman Inc., Abcam, Trevigen, Dojindo Molecular Technologies, Biovision, and Enzo Life Sciences.

The term "sample" includes any biological sample taken from the subject including cells, a tissue sample, or body fluid. For example, a sample may include a skin sample, a cheek cell sample, saliva, or blood cells. A sample can include, without limitation, a single cell, multiple cells, fragments of cells, an aliquot of a body fluid, whole blood, platelets, serum, plasma, red blood cells, white blood cells, endothelial cells, tissue biopsies, synovial fluid, and lymphatic fluid. In some embodiments, the sample is taken from a tumor.

In some embodiments, the mutation in the cancer biomarker is detected before administrating the composition to identify subjects predisposed to the disease. For example, women with a BRCA1 germline mutation are at a higher risk of contracting breast and ovarian cancer.

In some embodiments, the concentration of the cancer biomarker is measured before and after the administration. When the concentration of the cancer biomarker is maintained, the method may further comprise increasing the effective amount of the anticancer agent by at least 5%, at least 10%, or at least 30%, up to 50%, up to 60%, or up to 80% of an initial effective amount that is in a range of 1-100 mg/kg based on the weight of the subject. The increased effective amount may be in a range of 1.05-180 mg/kg, preferably 15-140 mg/kg, more preferably 25-90 mg/kg. The effective amount of the bioactive compound may be increased in line with the increase in the effective amount of the anticancer agent to minimize the toxicity resulting from a higher dose of the anticancer agent.

In some embodiments, the cancer biomarkers are measured/detected after the administering of each dose. For example, the measurement may be 1-5 minutes, 1-30 minutes, 30-60 minutes, 1-2 hours, 2-12 hours, 12-24 hours, 1-2 days, 1-15 weeks, 15-20 weeks, 20-30 weeks, 30-40 weeks, 40-50 weeks, 1 year, 2 years, or any period of time in between after the administration.

In some embodiments, the administration of the anticancer and/or the bioactive compound may be stopped once the subject is treated.

Another aspect of the disclosure relates to a method for treating toxicity resulting from cancer therapy (e.g., chemotherapy, radiotherapy, or immunotherapy) by administrating an effective amount of a bioactive compound, which is encapsulated by a biocompatible polymer, to a subject in need thereof.

The effective amount of the bioactive compound may be in a range of 0.1-1,000 mg/kg body weight of the subject, 10-600 mg/kg, or 50-200 mg/kg. The bioactive compound may be administered to the subject before, during, and/or after cancer therapy (e.g., chemotherapy). For example, the subject may be administered with the bioactive compound for up to 8 weeks, 6 weeks, or 2 weeks before the start of cancer therapy. The bioactive compound may be administered 1-6 times, or 2-3 times daily.

The bioactive compound is described above. In some embodiments, the combination of diindolylmethane and ellagic acid may exhibit synergy in treating cancer therapy-induced toxicity when compared to a subject administered with diindolylmethane alone or ellagic acid alone. For example, see Table 1. Examples of toxicity include, without limitation, peripheral neuropathy, nephrotoxicity, cardiotoxicity, pulmonary toxicity, blood toxicity, reproductive toxicity, dermal toxicity, hepatotoxicity, genotoxicity, and retinal toxicity. The toxicity may be apparent when the tissue is damaged and/or the gene(s) has mutations and may result in malfunctioning of the organ(s). In preferred embodiments, the toxicity is peripheral neuropathy and/or nephrotoxicity. The methods for diagnosing a &or quantifying peripheral neuropathy is described above.

Symptoms of cancer therapy-induced nephrotoxicity include, without limitation, excess urea in the blood (azotemia), anemia, increased hydrogen ion concentration in the blood (acidosis), excess fluids in the body (overhydration), and high blood pressure (hypertension). Cancer therapy-induced nephrotoxicity may be monitored by measuring the levels of the biomarkers such as serum creatinine (SCr), blood urea nitrogen (BUN), urinary kidney injury molecule-1 (KIM-1), neutrophil gelatinase-associated lipocalin (NGAL), interleukin-18 (IL-18), cystatin C, clusterin, fatty acid binding protein-liver type (L-FABP), nuclear factor kappa-light-chain-enhancer of activated B cells (NF-κB), and osteopontin. In a subject diagnosed with cancer therapy-induced nephrotoxicity, the level of serum creatinine and/or blood urea nitrogen may be at least 10%, 20%, or 30% higher than the level of the respective biomarker in a subject undergoing cancer therapy and being administered with the encapsulated bioactive compound. A level of serum creatinine in a subject without cancer therapy-induced nephrotoxicity may be 0.4-1.3 mg/dL, 0.5-1.2 mg/dL, 0.6-1.1 mg/dL. A level of blood urea nitrogen in a subject without cancer therapy-induced nephrotoxicity may be 5-20 mg/dL, 6-18 mg/dL, or 10-15 mg/dL. A subject without cancer therapy-induced nephrotoxicity may have a NF-κB level not more than 80%, 70%, 60%, 50%, 40%, or 30% of a NF-κB level in a subject experiencing cancer therapy-induced nephrotoxicity or peripheral neuropathy. The methods for determining the levels of the biomarkers are described above.

In some embodiments, the quantification of the neuropathy/nephrotoxicity biomarker and/or the diagnosis of neuropathy may be performed before and/or after the administration of the bioactive compound. In some embodiments, the peripheral neuropathy/nephrotoxicity biomarkers are measured/detected after the administering of each dose of bioactive compound. For example, the measurement may be 1-5 minutes, 1-30 minutes, 30-60 minutes, 1-2 hours, 2-12 hours, 12-24 hours, 1-2 days, 1-15 weeks, 15-20 weeks, 20-30 weeks, 30-40 weeks, 40-50 weeks, 1 year, 2 years, or any period of time in between after the administration.

Another aspect of the disclosure relates to a method of inhibiting the growth/reducing the viability of cancer cells in vitro by contacting the bioactive compound, which is encapsulated by the biocompatible polymer, with the cancer cells.

In some embodiments, the ability of the bioactive compound to reduce the viability of cancer cells may be determined by contacting a cytotoxic effective amount of the bioactive compound with the cancer cells and then performing cell viability assays. Examples of such assays include, without limitation, ATP test, calcein AM assay, clonogenic assay, ethidium homodimer assay, Evans blue assay, fluorescein diacetate hydrolysis/propidium iodide staining assay, flow cytometry assay, formazan-based assays (MTT, XTT), green fluorescent protein assay, lactate dehydrogenase assay, methyl violet assay, propidium iodide assay, Resazurin assay, trypan blue assay and TUNEL assay. In a preferred embodiment, a MTT assay is used.

The cytotoxic effective amount of the bioactive compound may be in a range of 0.01-200 μM, 1-150 μM, 10-100 μM, or 30-100 μM. As used herein, the term "cytotoxic effective amount" refers to a concentration of the bioactive compound that reduces the viability of the cancer cells by at least 5%, 10%, 15%, 20%, 30%, 40%, 50%, 60%, 70%, 80% or 90%, relative to cancer cells not treated with the bioactive compound. The reduction in viability may occur not more than 10 days, 7 days, 5 days, 3 days, or 2 days after the bioactive compound is contact with the cancer cells. In one embodiment, the cytotoxic effective amount may be the $IC_{50}$ which is a concentration of the bioactive compound which causes the death of 50% of cancer cells in 24 hours (1 day).

In at least one embodiment, the cancer cells are human cancer cells. The cancer cells may be derived from commercial cell lines, such as HeLa cervical cancer cells, A549 lung cancer cells, HCT15 colon cancer cells, HCT8 or HRT8 colon cancer cells, HCT116 colon cancer cells, DLD1 colon cancer cells, MCF7 breast cancer cells, MDA-MB231 breast cancer cells, A2780 ovarian cancer cells, HePG2 liver cancer cells, AsPC1 pancreatic cancer cells, PANC1 pancreatic cancer cells, SUIT2 pancreatic cancer cells, U87 glioma cells, and DU145 prostatic cancer cells. In some embodiments, cisplatin-resistant cancer cells are used. These cells may be cultured with low doses of cisplatin in order to build resistance to cisplatin while maintaining cell viability. Examples of cisplatin-resistant cancer cells include, but are not limited to, A2780-cis cisplatin-resistant ovarian cancer cells and SGC7901-cis cisplatin-resistant gastrointestinal cancer cells. In other embodiments, the human cancer cells are cancer cells of a human patient who has been diagnosed with at least one form of cancer, preferably breast cancer, pancreatic cancer, glioma, and/or colon cancer.

In some embodiments, the cancer cells may be transfected with the firefly luciferase gene and cell viability may be monitored with a bioluminescent assay. In some embodiments, the firefly luciferase gene may contain NF-κB response elements, which are DNA-binding sequences for the NF-κB transcription factor. In these embodiments, the effect of the bioactive compound and/or the anticancer agent on inhibition of NF-κB may be monitored with a bioluminescent assay.

Another aspect of this disclosure relates to a method of reducing tumor angiogenesis and/or tumor growth in a chick embryo chorioallantoic membrane (CAM). The method includes implanting cancer cells contacted with the encapsulated bioactive compound into the membrane. The cancer cells may be contacted with the encapsulated bioactive compound for not more than 5 minutes, 3 minutes, or preferably not more than 1 minute prior to the implantation. An amount of the bioactive compound may be 0.1-10 µg/embryo, 0.5-5 µg/embryo, or 1-3 µg/embryo. The cancer cells may be engineered to contain the firefly luciferase gene and the tumor growth may be measured with bioluminescence imaging. The chick embryo containing the implanted cancer cells may be incubated for 1-10 days, 2-7 days, or 3-4 days. After which, the embryo tissue may be resected and examined under a microscope. The bioactive compound may reduce tumor growth by more than 50%, 60%, 70%, 80%, 90%, or 95% compared to cancer cells which were not contacted with the bioactive compound.

The present embodiments are being described with reference to specific examples and are included to illustrate but not limit the scope of the invention.

Example 1 Cancer Cell Lines and Reagents

Human pancreatic cancer cell lines, SUIT2 expressing firefly luciferase, were provided by MD Anderson Cancer Center, Houston, Tex. Glioblastoma (U87), colon carcinoma cells (HT-29 and HCT-116), breast cancer cells (triple negative MDA-MB-231, MCF7, and MCF7 chemo-resistant), ovarian cancer cells (OVAR-3), and bladder cancer cells (253J-BV) were tested as well. Cell culture reagents and hemoglobin standard, Drabkin's reagent, ellagic acid, diindolylmethane, and other common reagents were purchased from Sigma (St. Louis, Mo.). D-Luciferin potassium salt was purchased from Caliper Life Sciences (Hopkinton, Mass.). Matrigel was purchased from BD Bioscience (San Jose, Calif.).

Example 2 Cells and Cell Culture Procedure

SUIT2-luc cells were grown in DMEM supplemented with 5% fetal bovine serum, 1% penicillin, and 1% streptomycin. Cells were cultured at 37° C. to sub-confluence and treated with 0.25% w/v typsin/EDTA to affect cell release from culture flask. After washing cells with culture medium, cells were suspended in DMEM (free of phenol red and fetal bovine serum) and counted.

Example 3 Synthesis of Nanocapsules

PLGA-PEG nanocapsules encapsulating ellagic acid (EA) and/or diindolylmethane (DIM) were prepared by double emulsion/solvent evaporation methods previously described (Bharali D J, Sahoo S K, Mo radar S, Maitra A. Cross-linked polyvinylpyrrolidone nanocapsules: a potential carrier for hydrophilic drugs. J Colloid Interface Sci. 2003 Feb. 15; 258(2):415-23; and Khalil N M, do Nascimento T C, Casa D M, Dalmolin L F, de Mottos A C. Hoss I, Romano M A, Mainandes R M. Pharmacokinetics of curcumin-loaded PLGA and PLGA-PEG blend nanocapsules after oral administration in rats. Colloids Surf B Biointerfaces. 2013 Jan. 1; 101:353-60, each incorporated herein by reference in their entirety). The molecular weight of PLGA (70% poly L-lactic: 30% polyglycolic acid) ranged from 4,000-12,000 Dalton and the PEG molecular weight ranged from 400-4,000 Dalton. PLGA was preferred because it is bio-degradable, safe and FDA approved. Briefly, a stock solution of PLGA-PEG polymer was prepared by dispersing 80 mg/ml of the copolymer in dichloromethane. A stock solution of 10 mg/ml of EA or DIM was prepared by dissolving EA or DIM in dichloromethane. Five hundred µl of each stock solution was mixed together by vortexing. Then, 1 ml of this solution, containing of 40 mg/ml PEG-PLGA and 5 mg/ml EA or DIM, was mixed with 200 µL of PBS by intermittent sonication (2-3 times, 30 sec each time) to obtain primary emulsion. The primary emulsion was then intermittently emulsified by sonication (30 s) in 2 ml of 1% w/v PVA solution. This water-in-oil-in-water emulsion was then added to 40 ml of 1.0% PVA solution and stirred for 30 min under constant magnetic stirring. Immediately after, dichloromethane was evaporated at 37° C. using a rotatory evaporator. The whole solution was then dialyzed using 10-12 kDa dialysis membrane against water for 24 hours to remove free non-encapsulated EA or DIM. The entire solution was lyophilized and re-dispersed, for further testing and use.

The lyophilized nanocapsules showed an average of 80% loading for DIM or EA based on high performance Liquid Chromatography (HPLC) analysis (i.e., recovering 4 mg into the dry NPs out of the 5 mg added from DIM and/or EA).

Example 4 Size Measurement by Dynamic Light Scattering

The size distribution of the nanocapsules containing EA and/or DIM in an aqueous dispersion was determined by dynamic light scattering (DLS) using a Malvern zetasizer (Malvern Instrumentation Co, Malvern, Pa.). After the re-dispersion of the lyophilized powder in deionized water, 1 ml of the nanocapsule solution was taken in 3 ml of a four size clear plastic cuvette and measured directly by the DLS.

Figure 1B:
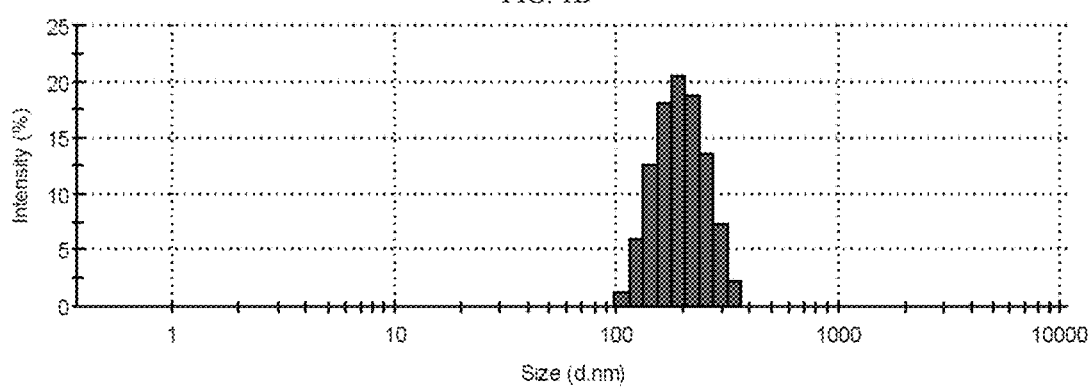
FIG. 1B shows the size distribution of nanocapsules containing PLGA-PEG and ellagic acid (EA).

FIG. 1A shows the average size of the nanocapsules containing DIM is 210 nm. FIG. 1B shows the average size of the nanocapsules containing EA is 180 nm.

The zeta potential of nanocapsules containing temozolomide (TMZ), PLEA-PEG, and optional. DIM and EA is −3.8 my. This zeta potential was shifted to a positive zeta potential upon addition chitosan, which has a zeta potential of +10 to +30 my, at PLGA-PEG:chitosan weight ratios of about 1:1 or about 1:2.

Example 5 Encapsulation of Cisplatin

The method of adsorption of anticancer agent to PLGA-PEG to which was added 0.5 ml of cisplatin (cis-diamine platinum (II) dichloride, Sigma-Aldrich, St. Louis, Mo.) dissolved as 10 mg/mL in ethyl acetate. The weight ratio of the polymer stock solution to the cisplatin stock solution was 50:10. Five mL of 1% polyvinyl alcohol (PVA) was then added and the resultant mixture was sonicated intermittently for 90 sec. Ten mL of 0.05% PVA was added and the mixture was sonicated for 1 min. The ethyl acetate was then removed at 45° C. for 20 min under vacuum in a rotary evaporator. Resulting nanocapsules (PLGA-PEG encapsulating cisplatin along with DIM and/or EA) were characterized in terms of size and surface charge using dynamic light scattering (DLS). The amount of cisplatin encapsulated in the nanocapsules was determined by disintegrating the nanocapsules and then calculating the entrapment efficiency using the following formula:

$$\text{Entrapment efficiency(loading)} = ([\text{cisplatin}]_f / [\text{cisplatin}]_t) \times 100$$

where $[\text{cisplatin}]_f$ is the concentration of cisplatin in the nanocapsules, and $[\text{cisplatin}]_t$ is the theoretical concentration of cisplatin (i.e., the total amount of cisplatin added initially).

The entrapment efficiency for cisplatin ranged from 60-80%, with a net 15-20% loading into the nanocapsules with PLGA-PEG or PLEA-PEG/chitosan.

Example 6 Encapsulation of Doxorubicin

The method of adsorption of anticancer agent to PLGA-PEG to which was added 0.5 ml of chemotherapeutic drug, dissolved as 10 mg/mL in ethyl acetate. Five mL of 1% polyvinyl alcohol (PVA) was then added and the resultant mixture was sonicated intermittently for 2 minutes. Ten mL of 0.05% PVA was added and the mixture was sonicated for 1 min. The ethyl acetate was removed by dialysis using a 12 kDa cutoff membrane dialysis tubing. The water was changed several times. The entire solution was freeze dried using a 2:1 sucrose solution and re-dispersed in water. Resulting nanocapsules (PLGA-PEG encapsulating doxorubicin and/or DIM/EA) were characterized in teams of size and surface charge using dynamic light scattering (DLS). The amount of doxorubicin encapsulated in the nanocapsules was determined by disintegrating the nanocapsules and using UV-Vis spectroscopy to measure doxorubicin (absorbance at $\lambda$ 500 nm) compared to standard curves for drug concentrations. The entrapment efficiency was determined with the formula described in Example 5.

Example 7 MTT Cell Viability/Proliferation Assay

SUIT2 cells were subjected to treatment with unencapsulated DIM, unencapsulated EA, combinations thereof, and the nanocapsules containing DIM and/or EA at concentrations of the bioactive compounds ranging from 0.1 to 10 µg. Briefly, cells were seeded at a density of $10^4$ cells/well in 96-well plates, and then incubated with compounds and nanocapsules for 24 hours. Cell viability/proliferation was determined by MTT assay, as per the manufacturer's protocol. MTT solution was added to each well, and cells were further incubated for 4 hours at 37° C. The formed dye was solubilized by the addition of 50 µL of DMSO and incubated for 10 min at 37° C. The optical density of each well was determined using an ELISA plate reader at an activation wavelength of 570 nm and reference wavelength of 650 nm. The percentage of viable cells was determined by comparison to untreated control cells.

Figure 2:
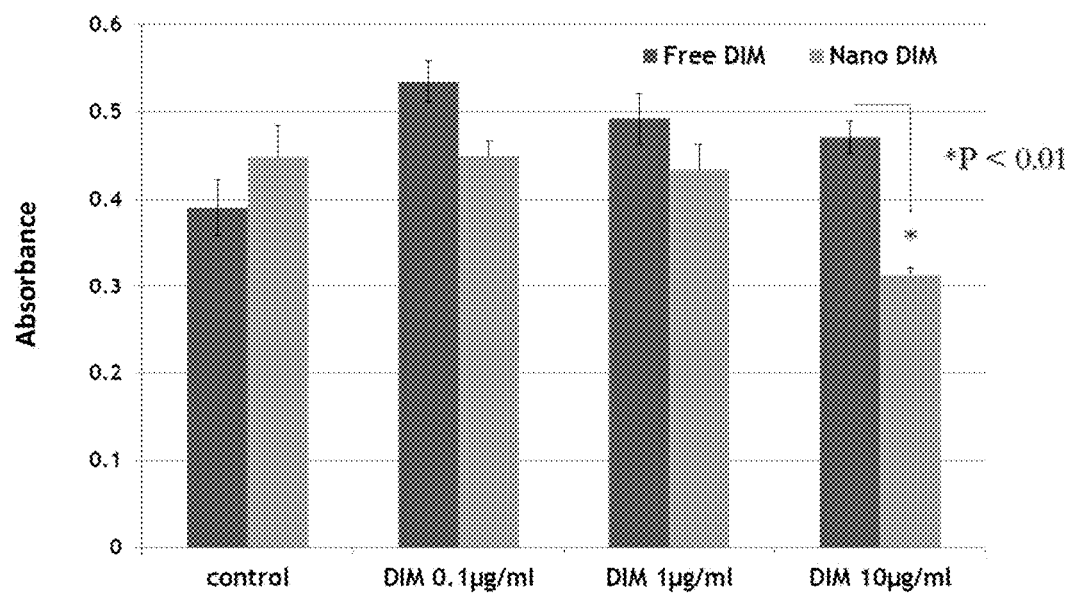
FIG. 2 shows the effect of unencapsulated. DIM (free DIM) versus nanocapsules containing PLGA-PEG and DIM on the cell viability/proliferation of pancreatic cancer cells after 24 hours.
Figure 3:
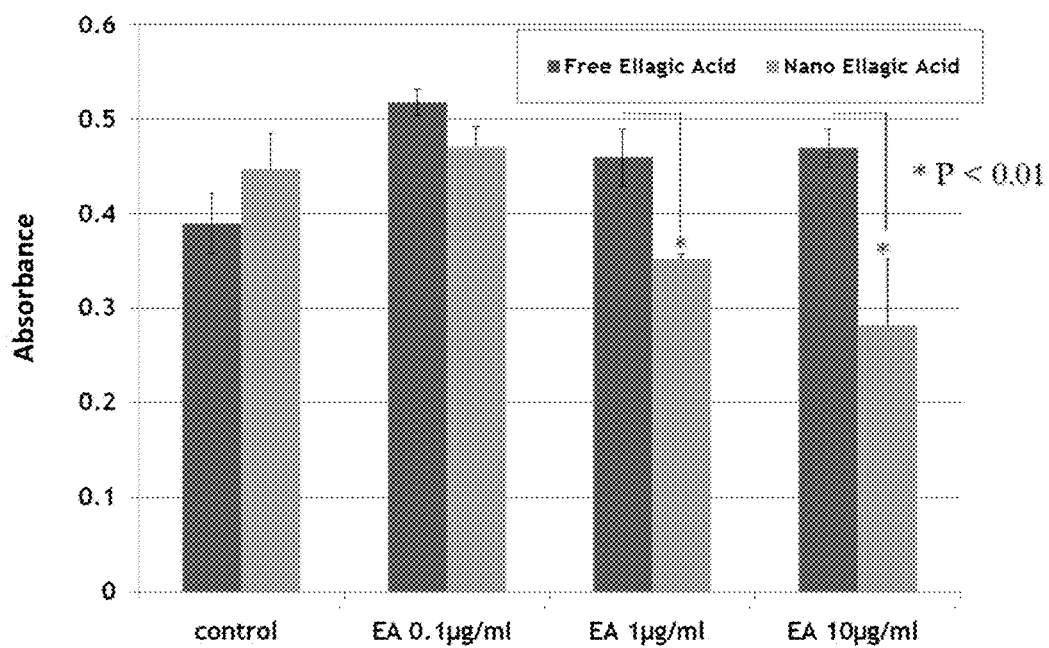
FIG. 3 shows the effect of unencapsulated EA (free EA) versus nanocapsules containing PLGA-PEG and EA on the cell viability/proliferation of pancreatic cancer cells after 24 hours.
Figure 4:
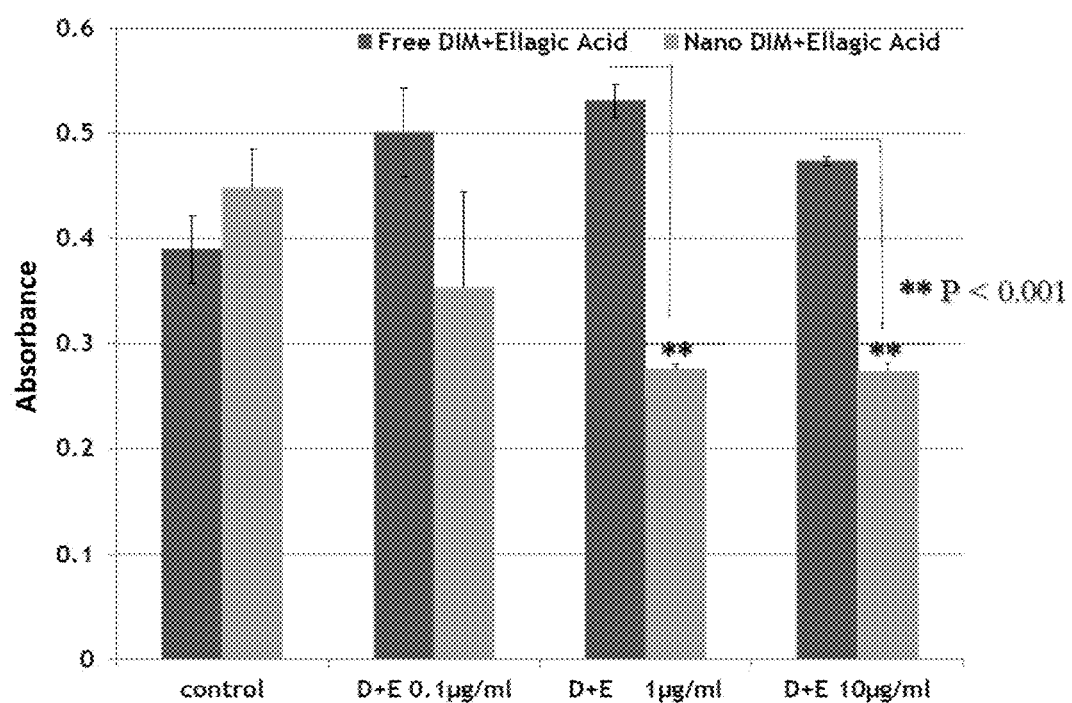
FIG. 4 shows the effect of unencapsulated DIM and EA (free DIM and EA) versus nanocapsules containing PLEA-PEG, DIM, and EA on the cell viability/proliferation of pancreatic cancer cells after 24 hours.
Figure 5A:
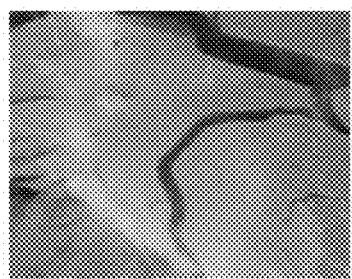
FIG. 5A is a photomicrograph showing the vascular pattern of an embryo ("control") in the chick chorioallantoic membrane (CAM) model.
Figure 5B:
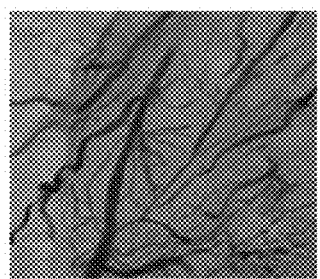
FIG. 5B is a photomicrograph showing the extensive vascular pattern of a pancreatic tumor in the CAM model after 3 days of incubation of controlled humidity and air conditions.
Figure 5C:
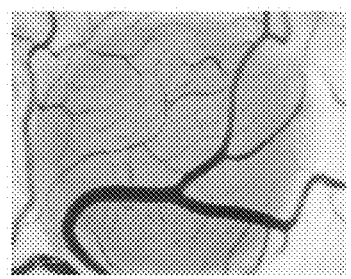
FIG. 5C is a photomicrograph showing the mild suppression for the vascular pattern of a pancreatic tumor contacted with unencapsulated EA in the CAM model after 3 days of incubation of controlled humidity and air conditions.
Figure 5D:
FIG. 5D is a photomicrograph showing the mild suppression for the vascular pattern of a pancreatic tumor contacted with unencapsulated DIM in the CAM model after 3 days of incubation of controlled humidity and air conditions.
Figure 5E:
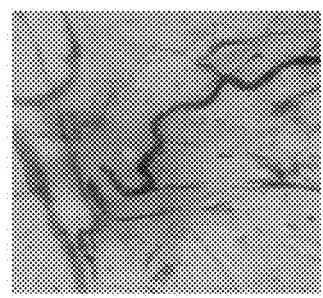
FIG. 5E is a photomicrograph showing the mild suppression for the vascular pattern of a pancreatic tumor contacted with unencapsulated DIM and EA in the CAM model after 3 days of incubation of controlled humidity and air conditions.
Figure 5F:
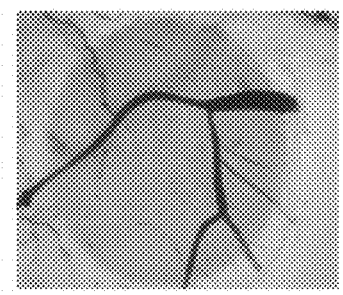
FIG. 5F is a photomicrograph showing the maximal suppression (100%) for the vascular pattern of a pancreatic tumor contacted with nanocapsules containing PLGA-PEG, DIM, and EA (EA NP+DIM NP) in the CAM model after 3 days of incubation of controlled humidity and air conditions.

FIGS. 2-4 show that nanocapsules containing DIM or EA resulted in a rapid suppression of pancreatic cancer cell viability/proliferation within 24 hours (P<0.01), while the non-encapsulated EA and DIM did not show any significant effect on SUIT2 cancer cell viability, cell proliferation at a dose of 1 µg/ml. The data represents the mean SD, and the sample size (n) is 3. The data shows 50% inhibition of pancreatic adenocarcinoma (SUIT2) at 1 µg/ml of nanoencapsulated DIM and EA and there was no significant effects on SUIT2 cell proliferation were observed when the cells were treated with free DIM and EA. Similar results were demonstrated in colon cells (HT-29, HCT-116). Inhibition of 50-60% at 1 of nanoencapsulated. DIM and EA was observed and no significant effects on HR-29 and HCT-116 cell proliferation were observed when the cells were treated with free DIM and EA. In glioblastoma U87 cells, 50-70% inhibition was achieved at 1 µg/ml of nanoencapsulated DIM and EA and no significant effects on U87 cell proliferation were observed when the cells were treated with free DIM and EA. In breast cancer cells, MDA-MB-231 and MCF-7, 50-70% inhibition was achieved at 1 µg/ml of nanoencapsulated DIM and EA and no significant effects on MDA-MB-23 I and MCF-7 cell proliferation were observed when the cells were treated with free DIM and EA.

Example 8 Tumor Growth in the CAM Cancer Implant Model

To determine the relative potency of different nanocapsules and unencapsulated bioactive compounds, they were tested in the CAM pancreatic cancer cell implant model of tumor growth and tumor angiogenesis by modifying published protocols (Marcinkiewicz C. Weinreb P H, Calvete J J, Kisiel D G, Mousa S A, Tuszynski G P, Lobb R R. A Potent Selective Inhibitor of alpha1beta1 Integrin in Vitro and Angiogenesis in Vivo. Cancer Res. 2003; 63(9): 2020-2023; and Deryugina E I and Quigley J P: Chick Embryo Chorioallantoic Membrane Models to Quantify Angiogenesis induced by inflammatory and tumor cells or purified effector molecules. Methods in Enzymol. 2008; 444: 21-41, each incorporated herein by reference in their entirety).

A 7-day old chick embryo were purchased from Spafas, Inc. (Preston, Conn.) and incubated at 37° C. with 55% relative humidity. A hypodermic needle was used to make a small hole in the shell at the air sac and a second hole will be made on the broadside of the egg, directly over an avascular portion of the embryonic membrane that was identified by candling. A false air sac was created beneath the second hole by the application of negative pressure at the first hole, causing the CAM to separate from the shell. A window, approximately 1.0 $cm^2$, was cut in the shell over the dropped CAM with a small crafts grinding wheel (Dermal, Division of Emerson Electric Co., Racine, Wis.), allowing direct access to the underlying CAM. Briefly, SUIT2-Luc Co cells were implanted at 1 million cells/CAM in Matrigel at the 7-day old fertilized chick egg. Treatment effects (Tumor growth, and tumor angiogenesis were determined 7 days after tumor cell implantation. For these studies, Matrigel® (BD Bioscience, San Jose Calif.) were thawed overnight at 4° C. and placed on ice. Cells in exponential growth phase were harvested using 0.25% trypsin-EDTA washed and suspended in medium. Only suspensions of single cells with a viability exceeding 95% were used. Approximately $1\times10^6$ cells in 30 µL of medium mixed with same volume (30 µL) of Matrigel was implanted on the chorioallantoic membrane.

Example 9 Microscopic Analysis of CAM Sections

After incubation at 37° C. with 55% relative humidity for 3 days, the CAM tissue directly beneath each filter disk was resected from control and treated CAM samples. Tissues were washed 3 times with PBS, placed in 35-mm Petri dishes (Nalge Num, Rochester, N.Y.) and examined under an SV6 stereomicroscope (Karl Zeiss, Thornwood, N.Y.) at 50× magnification. Digital images of CAM sections exposed to filters were collected, using a 3-CCD color video c vera system (Toshiba America, New York, N.Y.), and analyzed with Image-Pro software (Media Cybernetics, Silver Spring, Md.). The numbers of vessel branch points contained in a circular region equal to the area of each filter disk were counted. One image was counted in each CAM preparation, and findings from 6-8 CAM preparations group were analyzed for each treatment condition.

Results presented as mean tumor weight (mg) per treatment group and tumor hemoglobin (mg/dl)±SD, n=8 eggs per group. The effect of these treatments was determined after 7 days of implantation. Results are presented as a mean tumor weight (g) per treatment group and tumor hemoglobin (mg/dl)±SD, n=8 per group.

The groups (n=8 per group) are as follow:
1. Control—Matrigel (PBS or Void NPs)
2. Matrigel/SUIT2 (PBS or Void NPs)
3. Matrigel/SUIT2+EA 1 μg/CAM
4. Matrigel/SUIT2+DIM 1 μg/CAM
5. Matrigel/SUIT2+EA+DIM 1 μg each/CAM
6. Matrigel/SUIT2+EA nanocapsules 1 μg/CAM
7. Matrigel/SUIT2+DIM nanocapsules 1 μg/CAM
8. Matrigel/SUIT2+EA nanocapsules+DIM nanocapsules 1 μg each CAM

*Dose of nanocapsules are based on EA or DIM equivalent

In the CAM pancreatic cancer cell implant model, a greater suppression of tumor angiogenesis (P<0.01; see FIG. 5), and tumor growth (P<0.01; see FIG. 6) were observed for DIM nanocapsules, EA nanocapsules, and their combinations (P<0.01) versus unencapsulated DIM, unencapsulated EA, and their combinations. The extent of suppression of tumor angiogenesis was significantly more when the embryos were treated with nanocapsules containing DIM and EA. Similar results were demonstrated with colon (HT-29), glioma (U87) and breast cancer (MCF-7) cells. Maximal inhibition ranged from 80-100% inhibition of colon (HT-29), glioma (U87) and breast cancer (MCF-7) tumor angiogenesis and tumor growth suppression was achieved. When the embryos were treated with unencapsulated DIM and/or EA, 30-50% inhibition was observed. Thus, the nanocapsules of DIM and/or EA resulted in a more effective suppression of pancreatic, colon, glioma, and breast cancer cell viability, tumor growth and tumor angiogenesis as compared to the parent bioactive compounds, highlighting the potential of encapsulating nature-derived bioactive compounds in enhancing their anticancer efficacy.

Example 10 Animal Study

Immunodeficient, female NCr nude mice aged 5-6 weeks and weighing between 18 and 20 were maintained under specific pathogen-free conditions and housed under controlled conditions of temperature (20-24° C.) and humidity (60-70%) and 12 h light/dark cycle with ad libitum access to water and food. Mice were allowed to acclimatize for 5 days prior to the start of study.

Example 11 Cancer Cell Implantations

Xenografts containing $1\times10^6$ to $2\times10^6$ tumor cells (e.g., pancreatic SUIT2, colon HT-29, glioblastoma U87, or breast cancer MCF-7 cells) were implanted subcutaneously in a mouse flank. There were 2 grafts mouse and there were 4 mice in each group (control, treatments using vehicle). DMSO or ethyl acetate used during the preparation of nanocapsules was totally removed by dialysis and the vehicle used to disperse the DIM or EA and their nanocapsule forms was phosphate buffered saline (PBS).

Tumors were excised at the end of the study from all treatment arms, which included control; DIM; EA; nanocapsule containing DIM; nanocapsule containing EA; nanocapsule containing DIM acid EA; nanocapsule containing cisplatin; nanocapsule containing doxorubicin; nanocapsule containing cisplatin, DIM, and EA; and nanocapsule containing doxorubicin, DIM, and EA. Tumor growth was measured.

Example 12 Bioluminescent Tumor Signal Study

As the tumors were developed from SUIT2 pancreatic cancer cells which expressed luciferase gene, bioluminescent signal intensity of the tumors were studied by an in vivo imaging system (Xenogen-IVIS Spectrum). Excised tumors from the membrane were incubated in D-luciferin (30 mg/ml) briefly and then imaged. Ex vivo imaging was performed to confirm the signal intensity in the tumors after the termination of the study. Photographic and luminescence images were taken at constant exposure time. Xenogen IVIS® Living Image software version 12 was used to quantify non-saturated bioluminescence in regions of interest. Light emission between $5.5\times10^6$ to $7.0\times10^{10}$ photons was assumed to be indicative of viable luciferase-labeled tumor cells while emissions below this range were considered as background. Bioluminescence was quantified as photons/second for each region of interest.

Figure 7:
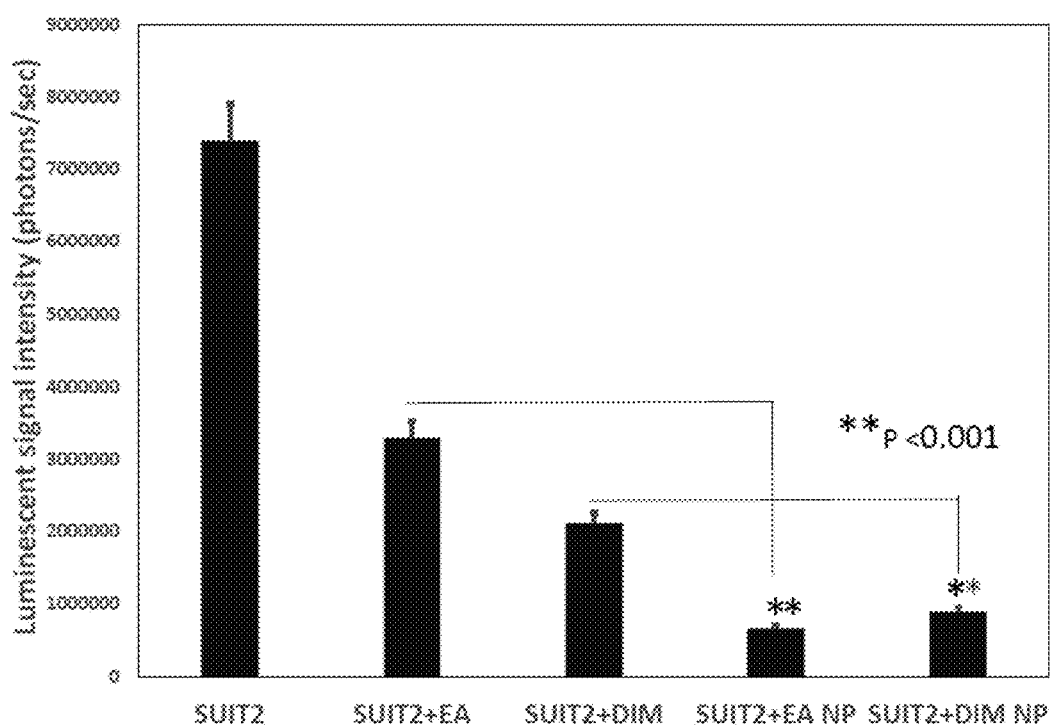
FIG. 7 shows the effect of unencapsulated DIM, unencapsulated EA, nanocapsules containing PLEA-PEG and DIM (DIM NP), and nanocapsules containing PLGA-PEG and EA (EA NP) on the viability of pancreatic cancer cells using IVIS imaging [luminescent signal intensity (photons/sec)] of pancreatic tumors implanted in the CAM model after 3 days of incubation of controlled humidity and air conditions.
Figures 8A, 8B:
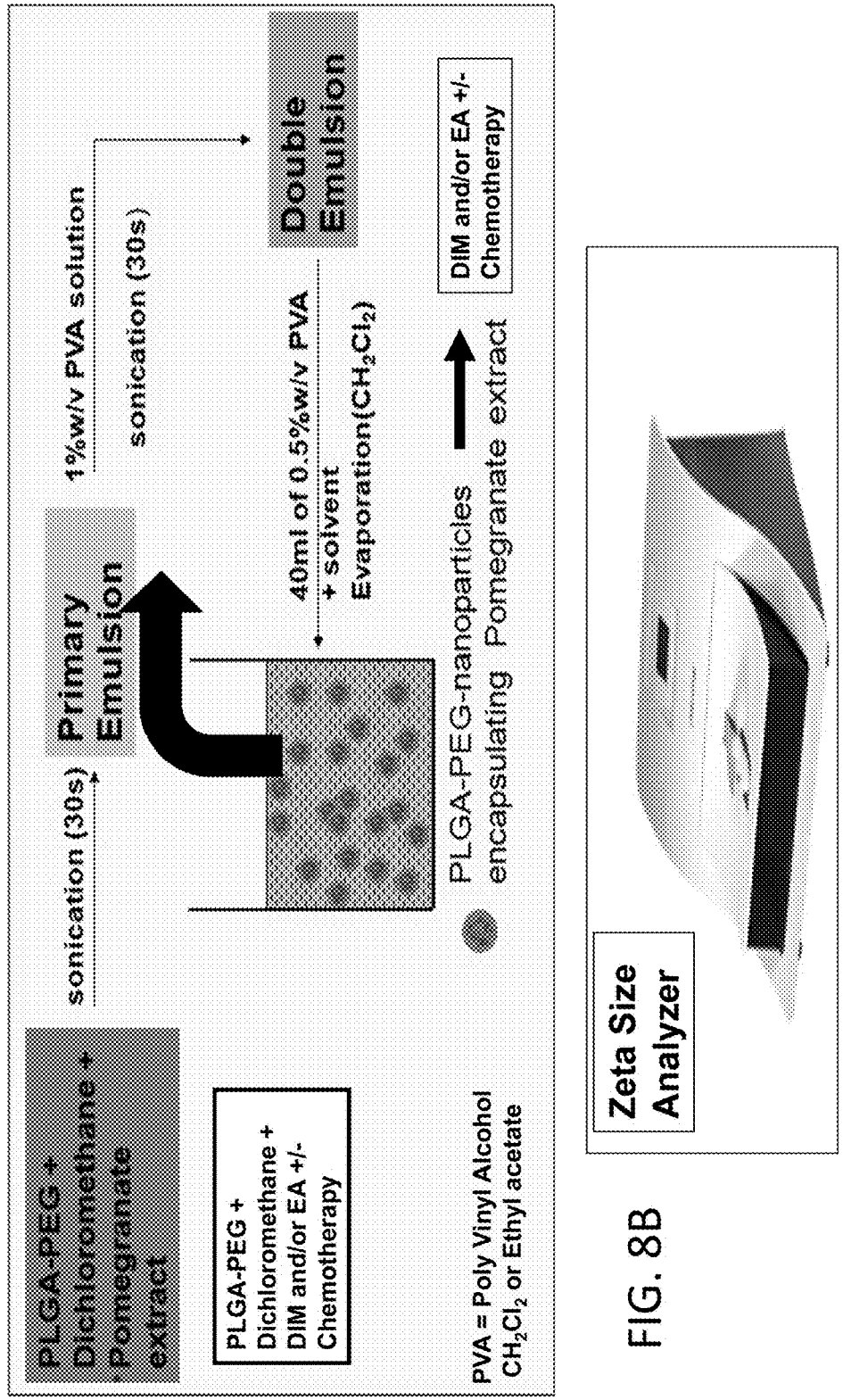
FIG. 8A is a flow chart showing the synthesis protocol for PLGA-PEG nanocapsules containing diindolymethane (DIM) and/or ellagic acid (EA) and optional anticancer agents.
FIG. 8B shows the zetasizer analyzer.
Figure 9B:
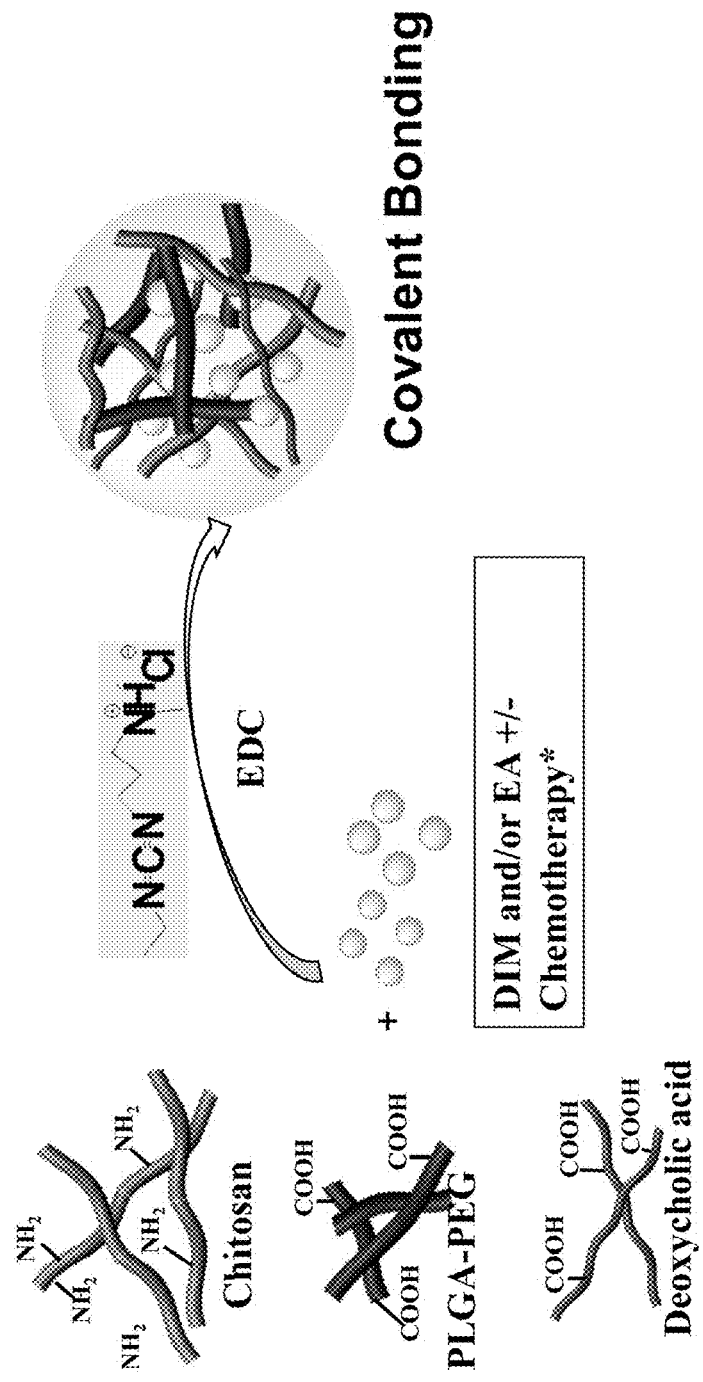
FIG. 9B illustrates the synthesis of nanocapsules containing diindolymethane (DIM) and/or ellagic acid (EA), optional anticancer agents, and PLEG-PEG bridged with chitosan and stabilized using deoxycholic acid or polyvinyl alcohol (PVA) via covalent bonding using 1-ethyl-3-(3-dimethylaminopropyl) carbodiimide (EDC).
Figure 10A:
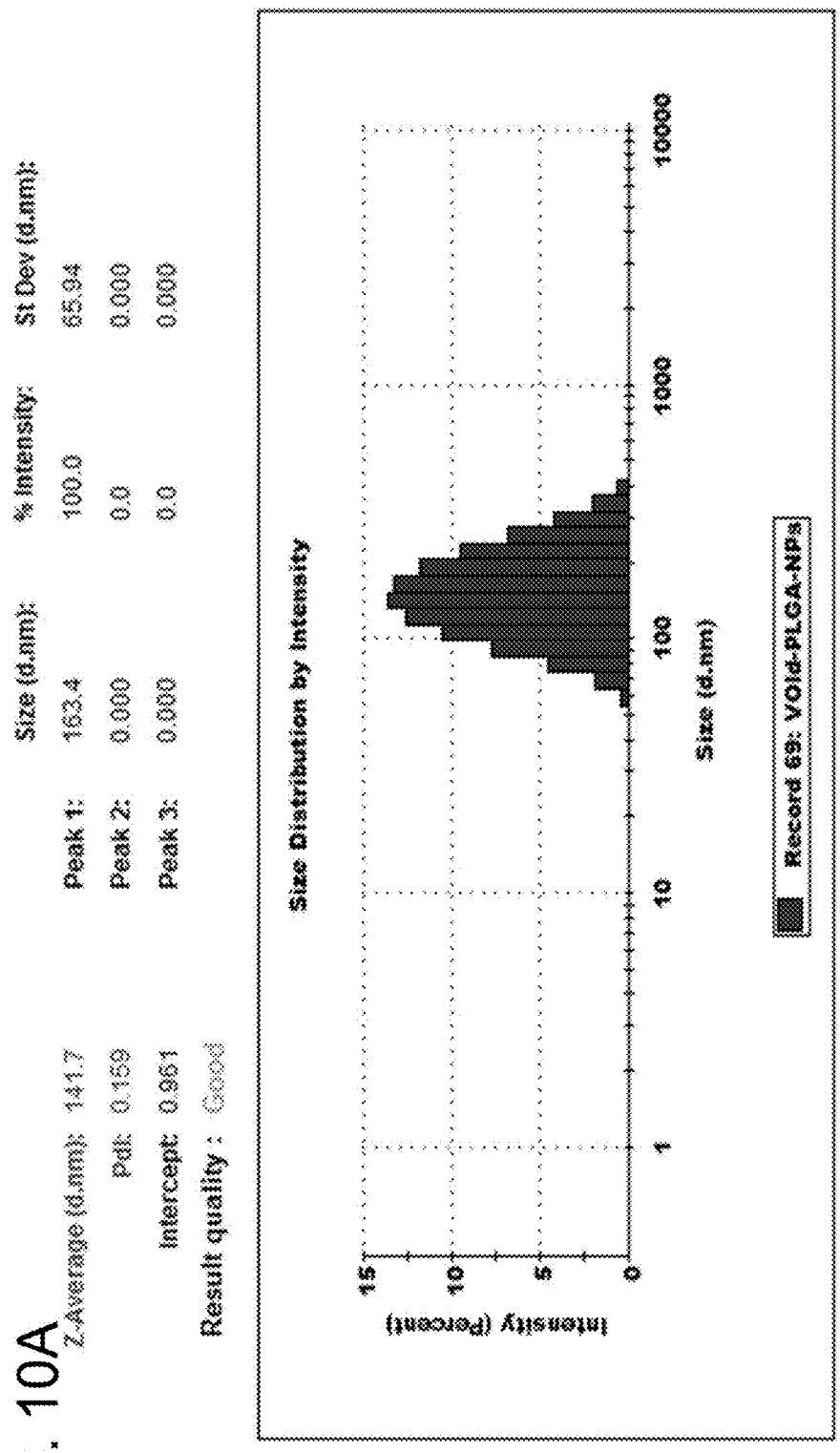
FIG. 10A shows the size distribution of nanocapsules containing poly(D,L-lactic-co-glycolic acid)-polyethylene glycol (PLEA-PEG) and without encapsulated bioactive compounds and/or anticancer agents.
Figure 10B:
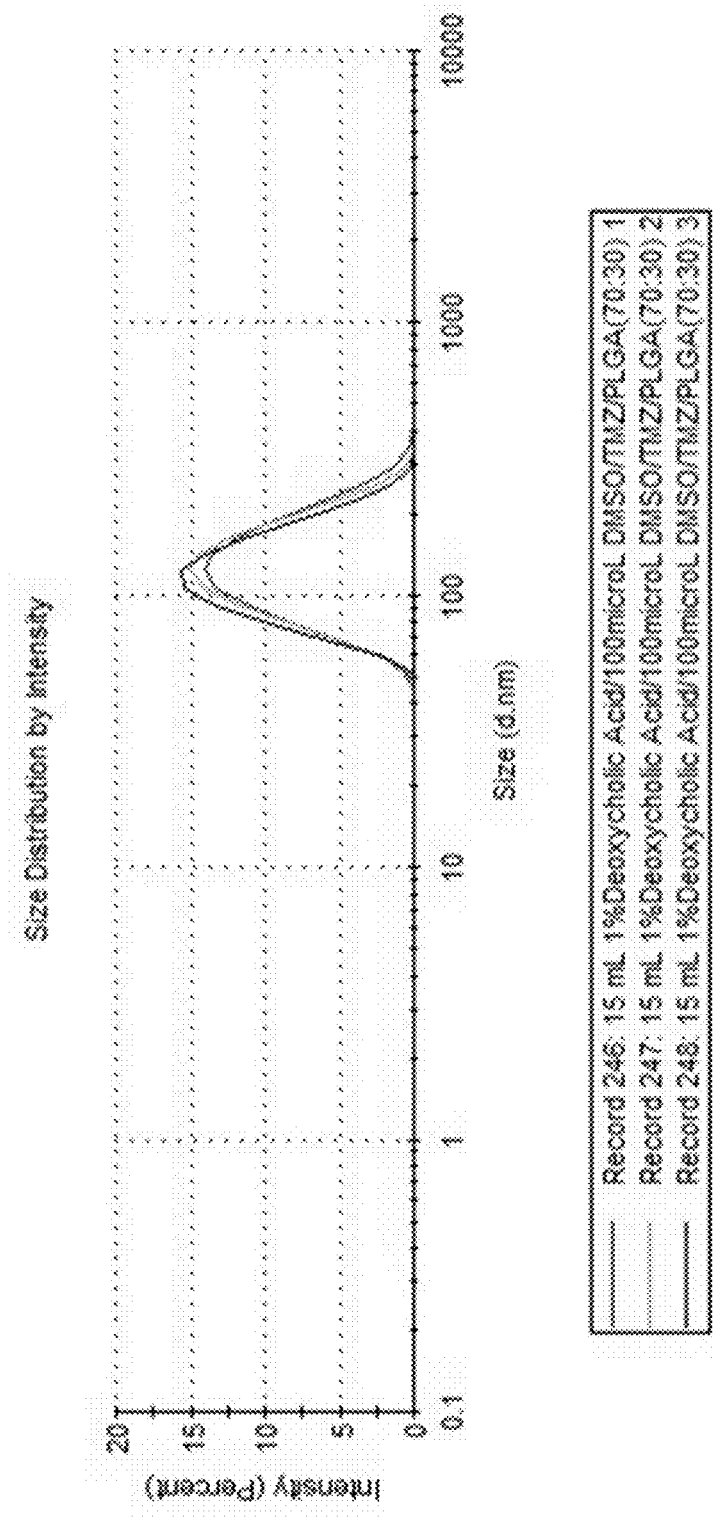
FIG. 10B shows the size distribution of 3 repeats of PLEA (70% lactic acid:30% glycolic acid)-PEG dissolved in DMSO with 1% deoxycholic acid as a stabilizer and temozolomide (TMZ).
Figure 10C:
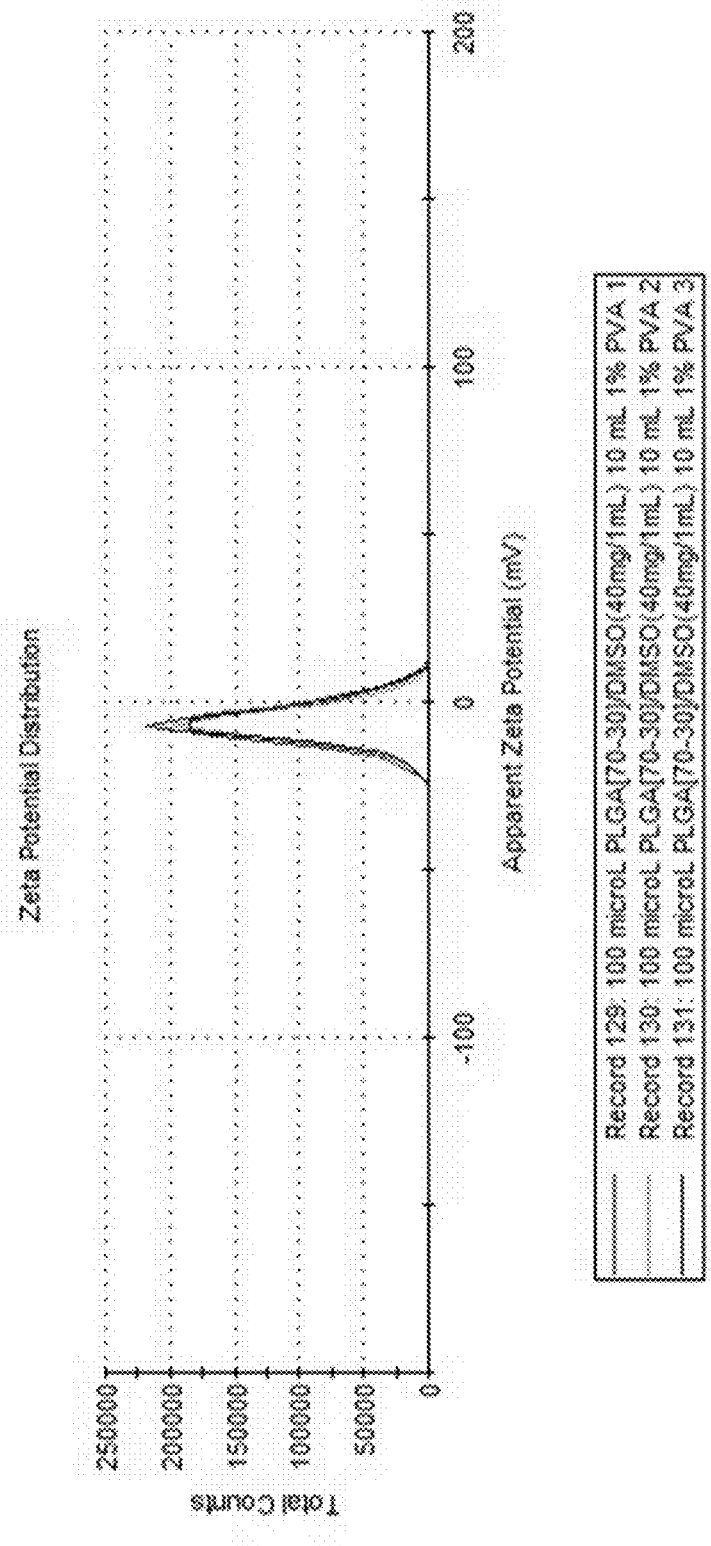
FIG. 10C shows the zeta potential for 3 repeats of PLGA (70% lactic acid:30% glycolic acid)-PEG dissolved in DMSO with 1% PVA as stabilizer and without encapsulated bioactive compounds and/or anticancer agents.
Figure 10D:
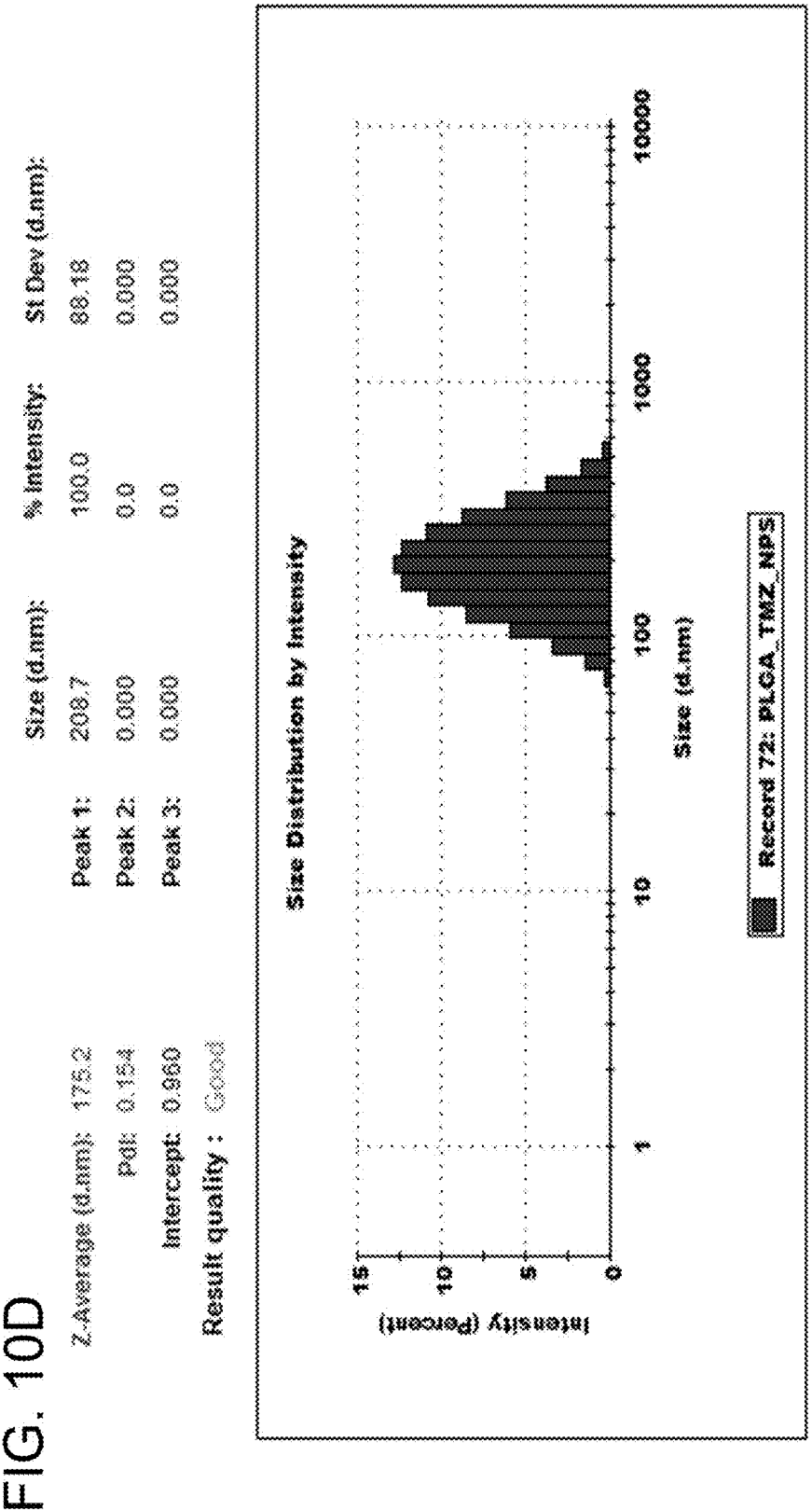
FIG. 10D shows the size distribution of nanocapsules containing poly(D,L-lactic-co-glycolic acid)-polyethylene glycol (PLGA-PEG) and TMZ.
Figure 10E:
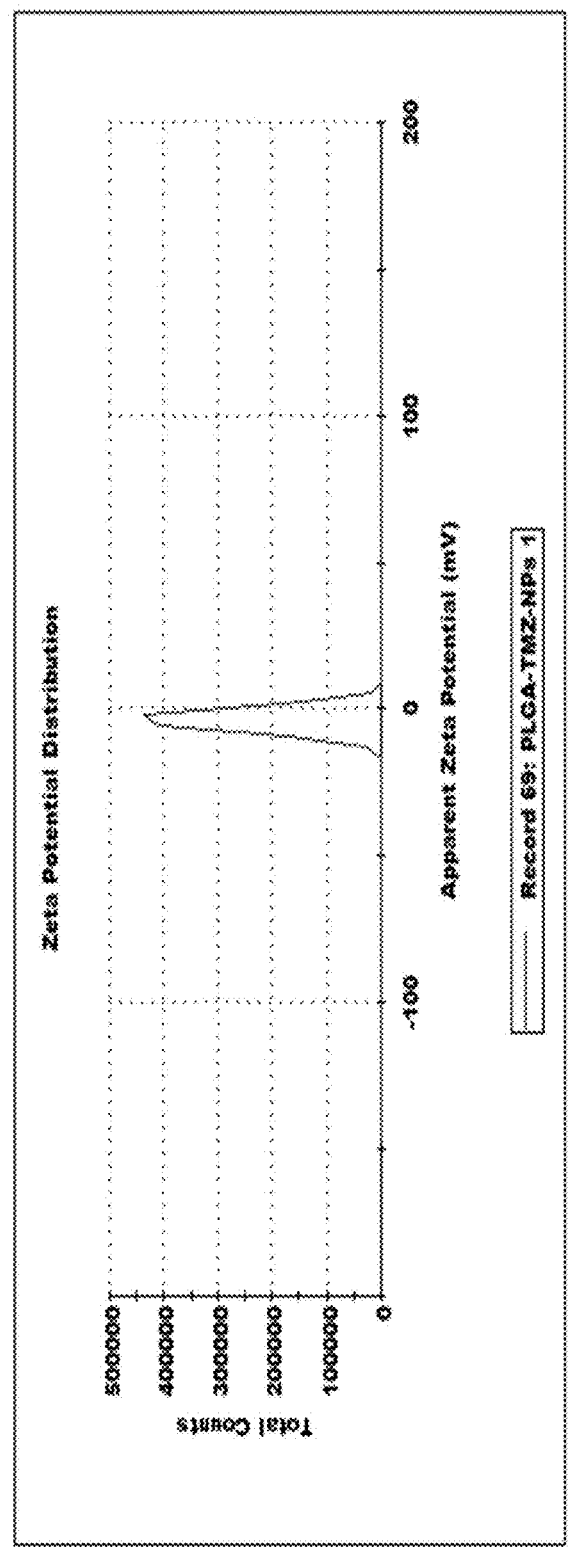
FIG. 10E shows the zeta potential of nanocapsules containing poly(D,L-lactic-glycolic acid)-polyethylene glycol (PLGA-PEG) and TMZ.
Figure 10F:
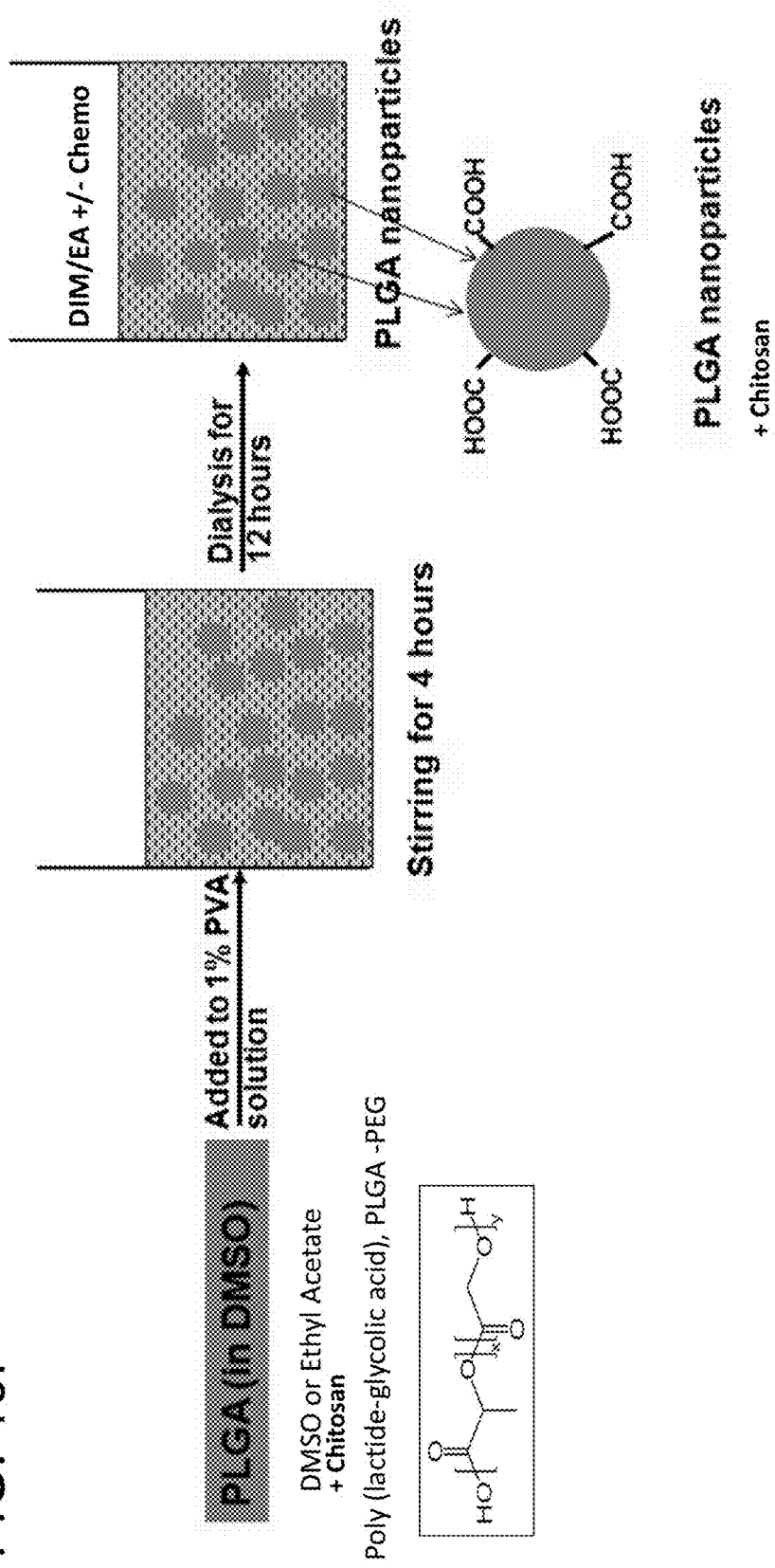
FIG. 10F is a flow chart showing the synthesis protocol for nanocapsules containing PLGA-PEG, chitosan, DIM and/or EA, and optional anticancer agents.
Figure 10I:
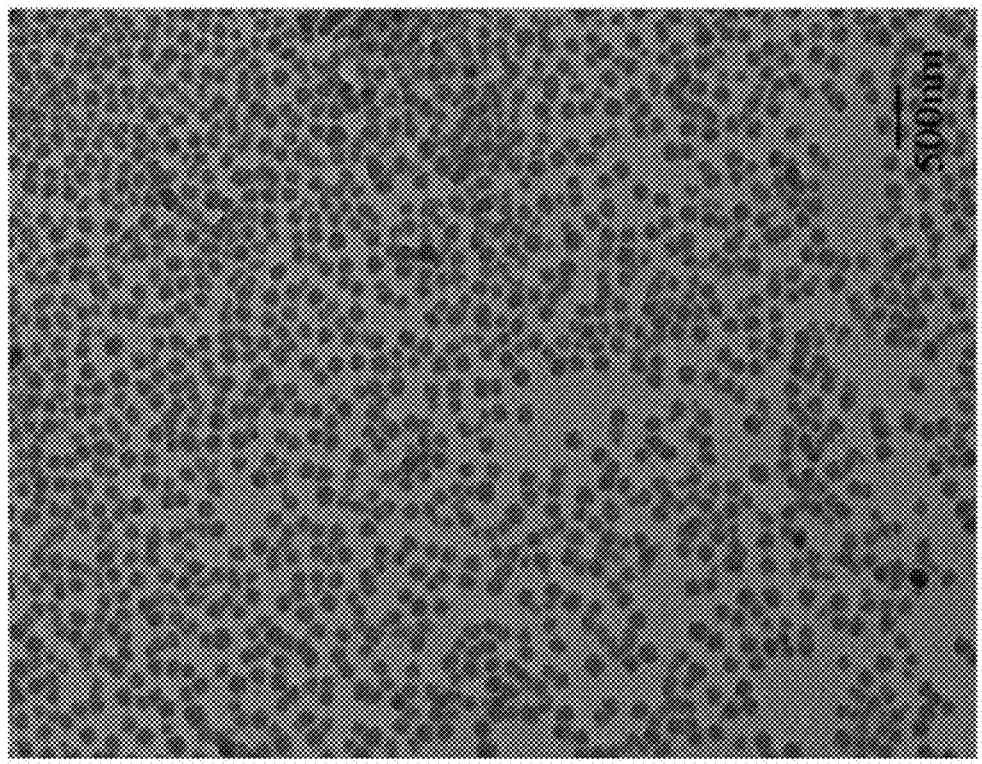
FIG. 10I is a transmission electron micrograph of the nanocapsules containing poly(D,L-lactic-co-glycolic acid)-polyethylene glycol (PLGA-PEG), chitosan, and diindolylmethane (DIM).

Bioluminescence was quantified (photons/second) for the different groups using Xenogen-IVIS Spectrum for viable cancer cell image intensity. Data showed statistically significant reduction (P<0.01) of viable pancreatic cancer cell groups treated with either unencapsulated EA or DIM as compared to control group (FIG. 7). This finding showed that phytochemicals derived from plant sources provide protection against various cancer-related processes at relatively high concentrations which may not be attainable when used as a supplement. Furthermore, pancreatic tumors treated with nanocapsules containing DIM or EA demonstrated greater suppression (P<0.001) of pancreatic cancer cell viability as compared to those treated with unencapsulated EA or DIM (FIG. 7).

Example 13 NF-κB Luciferase Assay

The induction of NF-κB by cisplatin and other chemotherapies is known to be associated with neuropathy and nephrotoxicity. In this example, the effect of unencapsulated DIM and EA, and the nanocapsules cisplatin-induced NF-κB was studied using HeLa cells which expressed NF-κB.

HeLa cells were seeded at $1\times10^5$ cells in 2 ml/well in 6-well plates at 37° C. for 24 hours. The doses of the test compounds were based on preliminary studies. Test compounds (nanocapsules containing DIM, nanocapsules containing E&, nanocapsules containing DIM and EA, unencapsulated DIM, and unencapsulated EA) were added at concentrations ranging from 1-3 μM to the plate with fresh medium including 0.5% FBS and incubated at 37° C. in 5% $CO_2$ for an additional 3 hours. For induction of transcription and to test the biological response of the promoters, the cell line stimulated with cisplatin (Sigma) and the cells were incubated at 37° C. in 5% $CO_2$ for 24 hours. The luciferase activity determined by using the luciferase assay system (Promega, Madison, Wis., US). In brief, after lysing the cells, 5 μL of cell lysate was transferred into a microcentrifuge tube and immediately followed by adding 50 μL of luciferase reagent into the each tube. Luminescence was immediately measured using Glomax 20/20 Illuminometer (Promega). Luciferase expression of each test compound was quantified as the relative light units (RLU), normalized to readings of control wells, and expressed as relative NF-κB reporter activity. The mean % inhibitory effects of the compounds were calculated.

The nanocapsules containing DIM and EA (in a weight ratio of 2:1) showed effective and synergistic inhibition of cisplatin-induced NF-κB (Table 1).

TABLE 1

Effect of unencapsulated bioactive compounds and nanocapsules containing bioactive compounds on cisplatin-induced NF-κB

| Compounds (3 μM) | Mean % inhibition of cisplatin-induced NFkB ± SD | P Value |
|---|---|---|
| DIM | 20 ± 5 | |
| Ellagic acid | 26 ± 4 | |
| DIM/Ellagic acid (3 μM total) | 33 ± 6* | P <0.05 (vs. DIM or EA) |
| Nano-DIM | 35 ± 7** | P <0.01 (vs. DIM) |
| Nano-Ellagic acid | 39 ± 5** | P <0.01 (vs. EA) |
| Nano-DIM/Ellagic acid (3 μM total) | 65 ± 7*** | P <0.001 (vs. all) |

Data represent mean ± Standard deviation, n = 3

Example 14 Statistical Analysis

Statistical analysis was performed using one-way ANOVA and comparing the mean±SD of branch points from each experimental group with its respective control group. Statistical differences approaching P<0.05 were considered statistically significant difference. In the CAM studies, the angiogenesis index for each treatment group were compared with the corresponding control group.

Example 15 Nanocapsules Containing Bioactive Compounds Ameliorate Chemotherapy-Induced Toxicity Nanocapsules containing cisplatin, DIM, and EA demonstrated greater anticancer efficacy in tumor bearing mice (pancreatic SUIT2 and colon HT-29 adenocarcinoma) and without any peripheral neuropathy as compared animals treated with unencapsulated (i.e., free) cisplatin.

Nanocapsules containing doxorubicin, DIM, and EA demonstrated greater anticancer efficacy in tumor bearing mice (breast cancer MCF-7) and without any effect on cardiac troponin levels as compared animals treated with free doxorubicin.

Nanocapsules containing temozolomide (TMZ), DIM, and EA demonstrated greater anticancer efficacy, in tumor-bearing mice with glioblastoma U87 when compared to mice treated with free (i.e., unencapsulated) TMZ.

Unencapsulated doxorubicin (DOX) resulted in a large increase in plasma cardiac troponin. The increase in plasma cardiac troponin was only slight in subjects treated with nanocapsules containing DOX, DIM, and EA (see Table 2).

TABLE 2

Effect of bioactive compounds on troponin levels

| Treatment Group | Mean Breast (MCF-7) Tumor Growth (g) | Troponin (% from control) |
|---|---|---|
| 1-Control (Vehicle) | 1.25 ± 0.25 | 0.00 |
| 2-DIM + EA (10 + 5 mg/kg, SC) nanocapsule | 0.90 ± 0.20* | 0.00 |
| 3-DOX (1 mg/kg, SC) | 0.70 ± 0.15** | +50-70%** |
| 4-DOX/DIM + EA | 0.45 ± 0.12*** | +1-10%** |

Data represent mean ± SEM, n = 4-5 animals/group, *P <0.05, P <0.01, and *P <0.001 versus control. Group 4 was shown to have statistically significant lower tumor growth versus DOX or DIM + EA. groups, with P <0.01.

The invention claimed is:

1. A nanocapsule, comprising:
   0.01-10 wt % of a combination of diindolylmethane and ellagic acid, based on a total weight of the nanocapsule; and
   a biocompatible polymer encapsulating the combination of diindolylmethane and ellagic acid;
   wherein an average diameter of the nanocapsule is in a range of 100-500 nm; and
   wherein the combination of diindolylmethane and ellagic acid is capable of synergistically inhibiting NF-κB and/or reducing cardiac troponin levels induced by an anticancer agent.

2. The nanocapsule of claim 1, wherein the average diameter of the nanocapsule is in a range of 130-300 nm.

3. The nanocapsule of claim 2, wherein the average diameter of the nanocapsule is in a range of 150-250 nm.

4. The nanocapsule of claim 1, wherein the biocompatible polymer is not polycaprolactone.

5. The nanocapsule of claim 1, wherein the biocompatible polymer comprises at least one selected from the group consisting of a poly(lactic-co-glycolic acid), a poly(ethylene glycol), a cyclodextrin, a polyvinyl alcohol, a chitosan, and a copolymer thereof.

6. The nanocapsule of claim 5, wherein the biocompatible polymer comprises poly(lactic-co-glycolic acid) and poly(ethylene glycol).

7. The nanocapsule of claim 6, wherein the biocompatible polymer is a diblock copolymer of poly(lactic-co-glycolic acid) and poly(ethylene glycol) or an alternating multiblock copolymer of poly(lactic-co-glycolic acid) and poly(ethylene glycol).

8. A method for treating neuropathy and/or nephrotoxicity associated with chemotherapy, comprising:
   administering an effective amount of the nanocapsule of claim 1 to a subject in need thereof.

9. The method of claim 8, wherein the chemotherapy comprises administering an effective amount of a platinum-based anticancer agent to the subject.

10. The method of claim 9, wherein the platinum-based anticancer agent is selected from the group consisting of cisplatin, carboplatin, and oxaliplatin.

11. The method of claim 8, wherein the effective amount corresponds to 0.1-300 mg/kg of the combination of diindolylmethane and ellagic acid per body weight of the subject.

12. The method of claim 11, wherein the effective amount corresponds to 1-100 mg/kg of the combination of diindolylmethane and ellagic acid per body weight of the subject.

13. The method of claim 8, wherein the biocompatible polymer comprises at least one selected from the group consisting of a poly(lactic-co-glycolic acid), a poly(ethylene glycol), a cyclodextrin, a polyvinyl alcohol, a chitosan, and a copolymer thereof.

14. The method of claim 13, wherein the biocompatible polymer comprises poly(lactic-co-glycolic acid) and poly(ethylene glycol).

15. A method for treating cancer, comprising:
   administering an effective amount of the nanocapsule of claim 1, and an effective amount of an anticancer agent to a subject in need thereof, wherein the administering reduces the likelihood and/or severity of neuropathy and/or cardiotoxicity in the subject.

16. The method of claim 15, wherein the anticancer agent is cisplatin and/or doxorubicin.

17. The method of claim 15, wherein the cancer is at least one selected from the group consisting of pancreatic cancer, colon cancer, glioma, and breast cancer.

18. The method of claim 15, wherein the biocompatible polymer comprises at least one selected from the group consisting of a poly(lactic-co-glycolic acid), a poly(ethylene glycol), a cyclodextrin, a polyvinyl alcohol, a chitosan, and a copolymer thereof.

* * * * *